(12) United States Patent
Hsu et al.

(10) Patent No.: US 10,358,918 B2
(45) Date of Patent: Jul. 23, 2019

(54) SCATTERING DETECTION FROM DOWNHOLE OPTICAL SPECTRA

(71) Applicant: Schlumberger Technology Corporation, Sugar Land, TX (US)

(72) Inventors: Kai Hsu, Sugar Land, TX (US); Kentaro Indo, Sugar Land, TX (US); Julian Pop, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 741 days.

(21) Appl. No.: 14/884,623

(22) Filed: Oct. 15, 2015

(65) Prior Publication Data

US 2016/0032721 A1 Feb. 4, 2016

Related U.S. Application Data

(63) Continuation of application No. 13/693,782, filed on Dec. 4, 2012, now Pat. No. 9,169,727.

(51) Int. Cl.
*E21B 49/08* (2006.01)
*E21B 49/10* (2006.01)
(Continued)

(52) U.S. Cl.
CPC .......... *E21B 49/081* (2013.01); *E21B 49/088* (2013.01); *E21B 49/10* (2013.01);
(Continued)

(58) Field of Classification Search
CPC ... G01N 21/534; G01N 29/032; G01N 29/348
(Continued)

(56) References Cited

U.S. PATENT DOCUMENTS 5,266,800 A 11/1993 Mullins
5,329,811 A 7/1994 Schultz et al.
(Continued)

FOREIGN PATENT DOCUMENTS

GB 2445209 A 7/2008
WO 2012108886 A1 8/2012

OTHER PUBLICATIONS

European Search Report issued in related EP application 13860663.7 dated Jul. 12, 2016, 4 pages.
(Continued)

*Primary Examiner* — Tarun Sinha

(57) ABSTRACT

Obtaining in-situ, at a first time, first optical spectral data associated with a formation fluid flowing through a downhole formation fluid sampling apparatus, and then obtaining in-situ, at a second time after the first time, second optical spectral data associated with the formation fluid flowing through the downhole formation fluid sampling apparatus. A wavelength-independent scattering intensity within the formation fluid flowing through the downhole formation fluid sampling apparatus is then determined based on the first and second optical spectral data, and a wavelength-dependent scattering intensity within the formation fluid flowing through the downhole formation fluid sampling apparatus is determined based on the first and second optical spectral data.

15 Claims, 14 Drawing Sheets

(51) Int. Cl.
*G01N 29/032* (2006.01)
*G01N 29/34* (2006.01)
*G01N 21/53* (2006.01)

(52) U.S. Cl.
CPC ......... *G01N 21/534* (2013.01); *G01N 29/032* (2013.01); *G01N 29/348* (2013.01)

(58) Field of Classification Search
USPC ...................................................... 73/152.24
See application file for complete search history.

(56) References Cited

U.S. PATENT DOCUMENTS

| | | | |
|---|---|---|---|
| 5,473,939 | A | 12/1995 | Leder et al. |
| 6,334,489 | B1 | 1/2002 | Shwe et al. |
| 6,350,986 | B1 | 2/2002 | Mullins et al. |
| 6,841,778 | B1 * | 1/2005 | Shifflett ............... G01N 21/33 250/339.01 |
| 7,222,524 | B2 | 5/2007 | Shammai |
| 7,336,356 | B2 | 2/2008 | Vannuffelen et al. |
| 7,346,460 | B2 | 3/2008 | DiFoggio et al. |
| 7,379,180 | B2 | 5/2008 | Vannuffelen et al. |
| 7,428,925 | B2 | 9/2008 | Brown et al. |
| 7,461,547 | B2 | 12/2008 | Terabayashi et al. |
| 7,644,610 | B2 | 1/2010 | Meister |
| 7,665,354 | B2 | 2/2010 | Shammai |
| 7,774,141 | B2 | 8/2010 | Li |
| 7,966,273 | B2 | 6/2011 | Hegeman et al. |
| 7,996,153 | B2 | 8/2011 | Niemeyer et al. |
| 8,024,125 | B2 | 9/2011 | Hsu et al. |
| 8,068,226 | B2 | 11/2011 | Csutak |
| 8,146,415 | B2 | 4/2012 | Cartellieri |
| 8,672,026 | B2 | 3/2014 | van Zuilekom et al. |
| 9,115,567 | B2 | 8/2015 | Hsu et al. |
| 2004/0231408 | A1 * | 11/2004 | Shammai ............... E21B 49/10 73/152.27 |
| 2004/0233446 | A1 | 11/2004 | Dong et al. |
| 2005/0016769 | A1 | 1/2005 | Wallace |
| 2005/0087368 | A1 | 4/2005 | Boyle et al. |
| 2005/0099618 | A1 | 5/2005 | DiFoggio et al. |
| 2005/0220431 | A1 | 10/2005 | Hainberger et al. |
| 2006/0214098 | A1 | 9/2006 | Ramos |
| 2007/0171412 | A1 | 7/2007 | Vannuffelen et al. |
| 2009/0288881 | A1 | 11/2009 | Mullins et al. |
| 2009/0303467 | A1 | 12/2009 | Ashdown et al. |
| 2010/0050760 | A1 | 3/2010 | Vannuffelen et al. |
| 2010/0258304 | A1 * | 10/2010 | Hegeman ............... E21B 47/10 166/250.01 |
| 2011/0048700 | A1 | 3/2011 | van Zuilekom et al. |
| 2011/0218736 | A1 | 9/2011 | Pelletier |
| 2011/0259581 | A1 | 10/2011 | Bedouet et al. |
| 2012/0018152 | A1 | 1/2012 | Zuilekom et al. |
| 2013/0167628 | A1 | 7/2013 | Hull et al. |
| 2013/0219997 | A1 * | 8/2013 | Sullivan ................. E21B 49/10 73/53.01 |
| 2014/0096955 | A1 | 4/2014 | Indo et al. |
| 2014/0096957 | A1 | 4/2014 | van Zuilekom et al. |
| 2014/0150545 | A1 | 6/2014 | Hsu et al. |
| 2014/0268156 | A1 | 9/2014 | Smythe et al. |
| 2015/0013968 | A1 | 1/2015 | Hsu et al. |

OTHER PUBLICATIONS

Article 94(3) EPC issued in related EP application 13860663.7 dated Sep. 8, 2016, 8 pages.
International Search Report and the Written Opinion for International Application No. PCT/US2013/068372 dated Feb. 12, 2014.
Fujisawa, G.; Mullins, O.; Dong, C.; Carnegie, A.; Betancourt, S.; Terabayashi, T.; Yoshida, S.; Jaramillo, A. And Haggag, M., "Analyzing Reservoir Fluid Composition In-Situ in Real Time: Case Study in a Carbonate Reservoir", Society of Petroleum Engineers, SPE 84092, presented at the SPE Annual Technical Conference and Exhibition held in Denver, Colorado, U.S.A., Oct. 5-8, 2003, pp. 1-9.
Venkataramanan, L.; Elshahawi, H.; McKinney D.; Flannery, M. and Hashem, M., "Downhole Fluid Analysis and Fluid Comparison Algorithm as an Aid to Reservoir Characterization", Society of Petroleum Engineers, SPE 100937, presented at the 2006 SPE Asia Pacific Oil & Gas Conference and Exhibition held in Adelaide, Australia, Sep. 11-13, 2006, pp. 1-16.
Dong, C.; O'Keefe, M.; Elshahawi, H.; Hashem, M.; Williams, S.; Stensland, D.; Hegeman, P.; Vasques, R; Terabayashi, T.; Mullins, O. and Donzier, E., "New Downhole-Fluid-Analysis Tool for Improved Reservoir Characterization", Society of Petroleum Engineers, SPE 108566, presented at Offshore Europe, Aberdeen, Sep. 4-7, 2008, pp. 1107-1116.
Efron, B. 1979. Bootstrap Methods: Another Look at the Jackknife. The Annals of Statistics 7 (1): 1-26.
Indo, K., Hsu, K., & Pop, J. J. (Apr. 1, 2015). Estimation of Fluid Composition From Downhole Optical Spectrometry. Society of Petroleum Engineers. doi:10.2118/166464-PA, pp. 1-13.
Mullins, O.C., Mitra-Kirtley, S. and Zhu, Y.: "The Electronic Absorption Edge of Petroleum," Applied Spectroscopy 46, No. 9 (1992), pp. 1405-1411.
"Oil Bubblepoint Pressure." Petrowiki. Accessed Oct. 15, 2015. http://petrowiki.org/Oil_bubblepoint_pressure, pp. 1-8.

* cited by examiner

SCATTERING DETECTION FROM DOWNHOLE OPTICAL SPECTRA

CROSS-REFERENCE TO RELATED APPLICATIONS

This application is a continuation application of and claims priority to U.S. patent application Ser. No. 13/693,782, entitled "SCATTERING DETECTION FROM DOWNHOLE OPTICAL SPECTRA," filed Dec. 4, 2012, the entire disclosure of which is hereby incorporated herein by reference.

BACKGROUND OF THE DISCLOSURE

Downhole fluid analysis (DFA) is often used to provide information in real time about the properties of subterranean formations or reservoir fluids. Such real-time information can be advantageously used to improve or optimize the effectiveness of formation testing tools during sampling processes in a given well, including sampling processes which don't return a captured formation fluid sample to the Earth's surface. For example, DFA allows for reducing and/or optimizing the number of samples captured and brought back to the surface for further analysis. Some known downhole fluid analysis tools such as the Live Fluid Analyzer (LFA), the Composition Fluid Analyzer (CFA) and the In-Situ Fluid Analyzer (IFA), which are each commercially available from Schlumberger Technology Corporation, can measure absorption spectra of formation fluids under downhole conditions. These fluid analyzers each provide ten channels that correspond to different wavelengths of light for a measured spectrum ranging from visible to near infrared wavelengths. The output of each channel represents an optical density (i.e., the logarithm of the ratio of incident light intensity to transmitted light intensity), where an optical density (OD) of zero (0) corresponds to 100% light transmission, and an OD of one (1) corresponds to 10% light transmission. The combined OD output of the channels provides spectral information that can be used in determining the composition and various other parameters of formation fluids.

SUMMARY

The present disclosure relates to a method that includes operating a downhole acquisition tool in a wellbore in a geological formation, wherein the wellbore or the geological formation, or both contain a fluid that comprises a native reservoir fluid of the geological formation and a contaminant. The method also includes receiving a portion of the fluid into the downhole acquisition tool and measuring a fluid property of the fluid using the downhole acquisition tool, wherein the fluid property includes a first optical density of a first portion of the fluid at a first wavelength and a second optical density of a second portion of the fluid at a second wavelength, wherein the first and second optical densities are measured at successive times. The method further includes using one or more processors to: determine a scattering intensity of the first and second portions of the fluid using the first and second optical densities, estimate a saturation pressure of the fluid using the scattering intensity, and adjust an operational parameter of the downhole acquisition tool based on a relationship between the operational parameter and the saturation pressure.

The present disclosure also relates to a downhole fluid testing system that includes a downhole acquisition tool housing configured to be moved into a wellbore in a geological formation, wherein the wellbore or the geological formation, or both, contain fluid that comprises a native reservoir fluid of the geological formation and a contaminant. The downhole fluid testing system also includes a sensor disposed in the downhole acquisition tool housing that is configured to analyze portions of the fluid and obtain a first fluid property of the portions of the fluid, wherein the first fluid property includes a first optical density at a first wavelength and a second optical density at a second wavelength. The downhole fluid testing system further includes a data processing system configured to estimate a saturation pressure of the fluid based at least in part on a scattering intensity of the first and second optical densities, and to adjust an operational parameter of the downhole acquisition tool based on a relationship between the operational parameter and the saturation pressure.

The present disclosure further relates to storage media including machine-readable instructions to receive a fluid parameter of a portion of fluid as analyzed by a downhole acquisition tool in a wellbore in a geological formation, wherein the wellbore or the geological formation, or both, contains the fluid, wherein the fluid comprises a mixture of native reservoir fluid of the geological formation and a contaminant, and wherein the fluid parameter includes a first optical density of a first portion of the fluid and a second optical density of a second portion of the fluid. The machine readable instructions also determine a scattering intensity of the first and second portions of the fluid, estimate a saturation pressure of the fluid based on the scattering intensity, and adjust an operational parameter of the downhole acquisition tool based on the saturation pressure.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
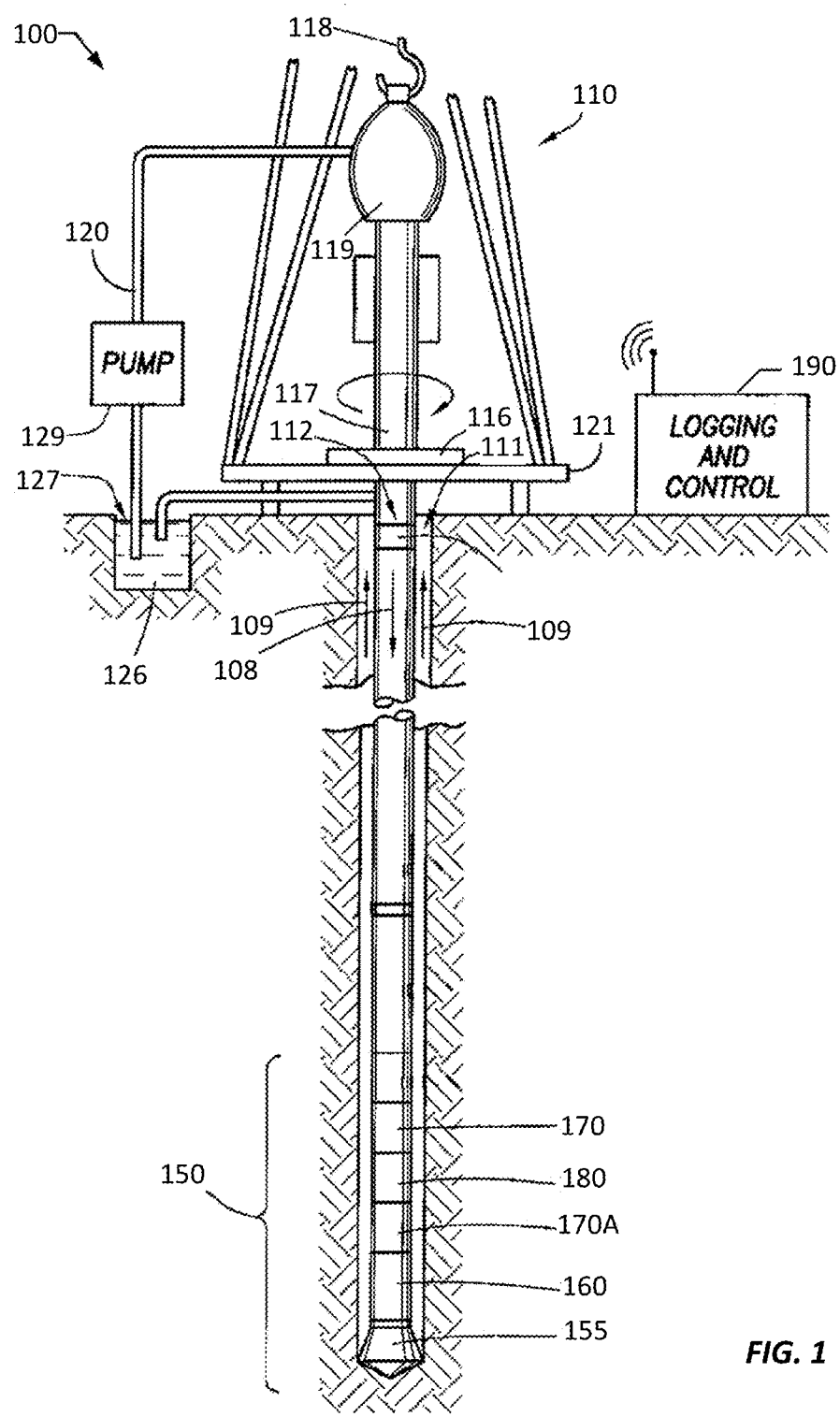
FIG. 1 is a schematic view of apparatus according to one or more aspects of the present disclosure.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed except where specifically noted as indicating a relationship. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

FIG. 1 is a schematic view of an example wellsite system 100 in which one or more aspects disclosed herein may be employed. The wellsite 100 may be onshore or offshore. In the example system shown in FIG. 1, a borehole 111 is formed in subterranean formations by rotary drilling. However, other example systems within the scope of the present disclosure may alternatively or additionally use directional drilling.

As shown in FIG. 1, a drillstring 112 suspended within the borehole 111 comprises a bottom hole assembly (BHA) 150 that includes a drill bit 155 at its lower end. The surface system includes a platform and derrick assembly 110 positioned over the borehole 111. The assembly 110 may comprise a rotary table 116, a kelly 117, a hook 118 and a rotary swivel 119. The drill string 112 may be suspended from a lifting gear (not shown) via the hook 118, with the lifting gear being coupled to a mast (not shown) rising above the surface. An example lifting gear includes a crown block whose axis is affixed to the top of the mast, a vertically traveling block to which the hook 118 is attached, and a cable passing through the crown block and the vertically traveling block. In such an example, one end of the cable is affixed to an anchor point, whereas the other end is affixed to a winch to raise and lower the hook 118 and the drillstring 112 coupled thereto. The drillstring 112 comprises one or more types of drill pipes threadedly attached one to another, perhaps including wired drilled pipe.

The drillstring 112 may be raised and lowered by turning the lifting gear with the winch, which may sometimes require temporarily unhooking the drillstring 112 from the lifting gear. In such scenarios, the drillstring 112 may be supported by blocking it with wedges in a conical recess of the rotary table 116, which is mounted on a platform 121 through which the drillstring 112 passes.

The drillstring 112 may be rotated by the rotary table 116, which engages the kelly 117 at the upper end of the drillstring 112. The drillstring 112 is suspended from the hook 118, attached to a traveling block (not shown), through the kelly 117 and the rotary swivel 119, which permits rotation of the drillstring 112 relative to the hook 118. Other example wellsite systems within the scope of the present disclosure may utilize a top drive system to suspend and rotate the drillstring 112, whether in addition to or as an alternative to the illustrated rotary table system.

The surface system may further include drilling fluid or mud 126 stored in a pit 127 formed at the wellsite. A pump 129 delivers the drilling fluid 126 to the interior of the drillstring 112 via a hose 120 coupled to a port in the swivel 119, causing the drilling fluid to flow downward through the drillstring 112 as indicated by the directional arrow 108. The drilling fluid exits the drillstring 112 via ports in the drill bit 155, and then circulates upward through the annulus region between the outside of the drillstring 112 and the wall of the borehole 111, as indicated by the directional arrows 109. In this manner, the drilling fluid 126 lubricates the drill bit 155 and carries formation cuttings up to the surface as it is returned to the pit 127 for recirculation.

The BHA 150 may comprise one or more specially made drill collars near the drill bit 155. Each such drill collar may comprise one or more logging devices, thereby allowing downhole drilling conditions and/or various characteristic properties of the geological formation (e.g., such as layers of rock or other material) intersected by the borehole 111 to be measured as the borehole 111 is deepened. For example, the BHA 150 may comprise a logging-while-drilling (LWD) module 170, a measurement-while-drilling (MWD) module 180, a rotary-steerable system and motor 160, and the drill bit 155. Of course, other BHA components, modules and/or tools are also within the scope of the present disclosure.

The LWD module 170 may be housed in a drill collar and may comprise one or more logging tools. It will also be understood that more than one LWD and/or MWD module may be employed, e.g., as represented at 170A. References herein to a module at the position of 170 may mean a module at the position of 170A as well. The LWD module 170 may comprise capabilities for measuring, processing and storing information, as well as for communicating with the surface equipment.

The MWD module 180 may also be housed in a drill collar and may comprise one or more devices for measuring characteristics of the drillstring 112 and/or drill bit 155. The MWD module 180 may further comprise an apparatus (not shown) for generating electrical power to be utilized by the downhole system. This may include a mud turbine generator powered by the flow of the drilling fluid 126, it being understood that other power and/or battery systems may also or alternatively be employed. In the example shown in FIG. 1, the MWD module 180 comprises one or more of the following types of measuring devices: a weight-on-bit measuring device, a torque measuring device, a vibration measuring device, a shock measuring device, a stick slip measuring device, a direction measuring device, and an inclination measuring device, among others within the scope of the present disclosure. The wellsite system 100 also comprises a logging and control unit 190 communicably coupled in any appropriate manner to the LWD modules 170/170A and/or the MWD module 180.

The LWD modules 170/170A and/or the MWD module 180 comprise a downhole tool configured to obtain downhole a sample of fluid from the subterranean formation and perform DFA to estimate or determine composition and/or other characteristics of the obtained fluid sample. Such DFA is according to one or more aspects described elsewhere herein. The downhole fluid analyzer of the LWD modules 170/170A and/or the MWD module 180, or another component of the BHA 150, may then report the composition data to the logging and control unit 190.

Figure 2:
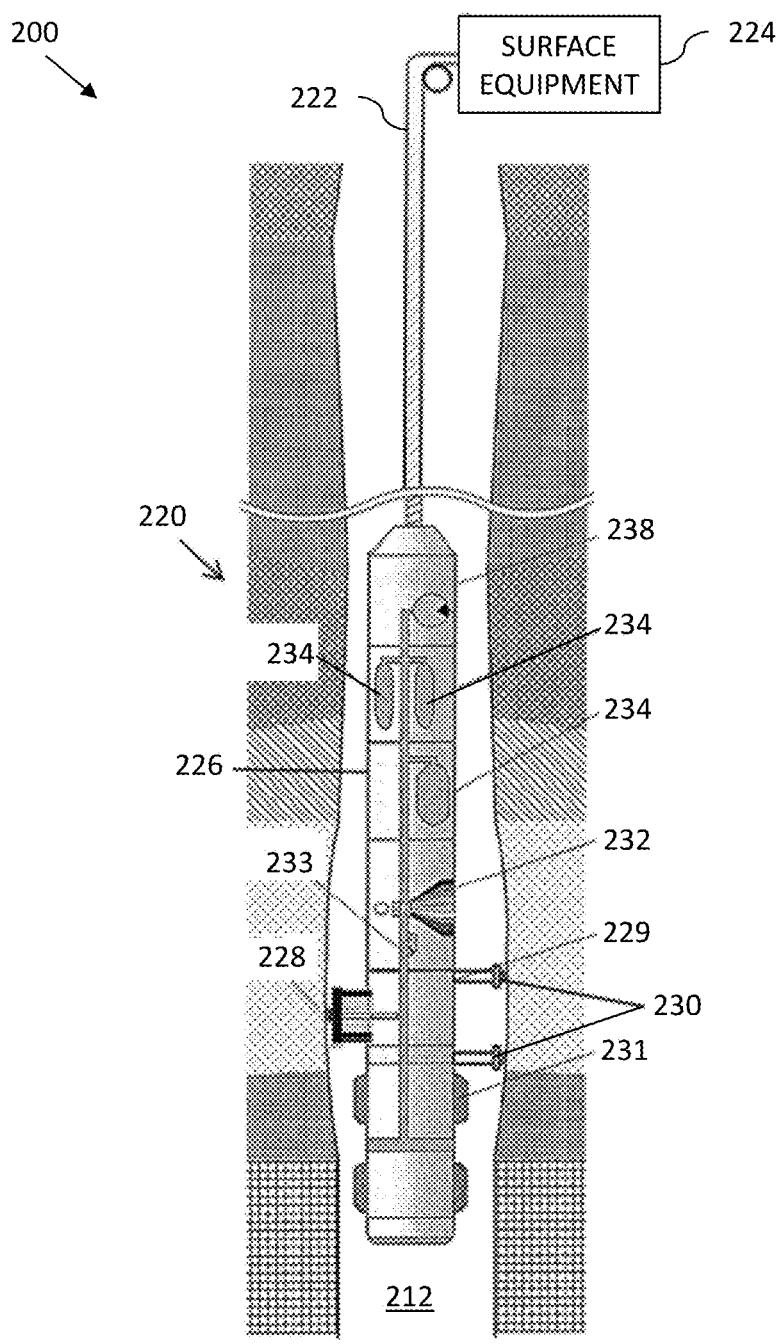
FIG. 2 is a schematic view of apparatus according to one or more aspects of the present disclosure.

FIG. 2 is a schematic view of another exemplary operating environment of the present disclosure wherein a downhole tool 220 is suspended at the end of a wireline 222 at a wellsite having a borehole 212. The downhole tool 220 and wireline 222 are structured and arranged with respect to a service vehicle (not shown) at the wellsite. As with the system 100 shown in FIG. 1, the exemplary system 200 of FIG. 2 may be utilized for downhole sampling and analysis of formation fluids. The system 200 includes the downhole tool 220, which may be used for testing earth formations and analyzing the composition of fluids from a formation, and also includes associated telemetry and control devices and electronics, and surface control and communication equipment 224. The downhole tool 220 is suspended in the borehole 212 from the lower end of the wireline 222, which may be a multi-conductor logging cable spooled on a winch (not shown). The wireline 222 is electrically coupled to the surface equipment 224.

The downhole tool 220 comprises an elongated body 226 encasing a variety of electronic components and modules, which are schematically represented in FIG. 2, for providing necessary and desirable functionality to the downhole tool 220. A selectively extendible fluid admitting assembly 228 and one or more selectively extendible anchoring members 230 are respectively arranged on opposite sides of the elongated body 226. The fluid admitting assembly 228 is operable to selectively seal off or isolate selected portions of the borehole wall 212 such that pressure or fluid communication with the adjacent formation may be established. The fluid admitting assembly 228 may be or comprise a single probe module 229 and/or a packer module 231.

One or more fluid sampling and analysis modules 232 are provided in the tool body 226. Fluids obtained from the formation and/or borehole flow through a flowline 233, via the fluid analysis module or modules 232, and then may be discharged through a port of a pumpout module 238. Alternatively, formation fluids in the flowline 233 may be directed to one or more fluid collecting chambers 234 for receiving and retaining the fluids obtained from the formation for transportation to the surface.

The fluid admitting assemblies, one or more fluid analysis modules, the flow path and the collecting chambers, and other operational elements of the downhole tool 220 may be controlled by one or more electrical control systems within the downhole tool 220 and/or the surface equipment 224. For example, such control system(s) may include processor capability for characterization of formation fluids in the downhole tool 220 according to one or more aspects of the present disclosure. Methods within the scope of the present disclosure may be embodied in one or more computer programs that run in a processor located, for example, in the downhole tool 220 and/or the surface equipment 224. Such programs may be configured to utilize data received from, for example, the fluid sampling and analysis module 232, via the wireline cable 222, and to transmit control signals to operative elements of the downhole tool 220. The programs may be stored on a suitable computer usable storage medium associated with the one or more processors of the downhole tool 220 and/or surface equipment 224, or may be stored on an external computer usable storage medium that is electronically coupled to such processor(s) for use as needed. The storage medium may be any one or more of known or future-developed storage media, such as a magnetic disk, an optically readable disk, flash memory or a readable device of any other kind, including a remote storage device coupled over a switched telecommunication link, among others.

FIGS. 1 and 2 illustrate mere examples of environments in which one or more aspects of the present disclosure may be implemented. For example, in addition to the drillstring environment of FIG. 1 and the wireline environment of FIG. 2, one or more aspects of the present disclosure may be applicable or readily adaptable for implementation in other environments utilizing other means of conveyance within the wellbore, including coiled tubing, pipe, slickline, and others.

Figure 3:
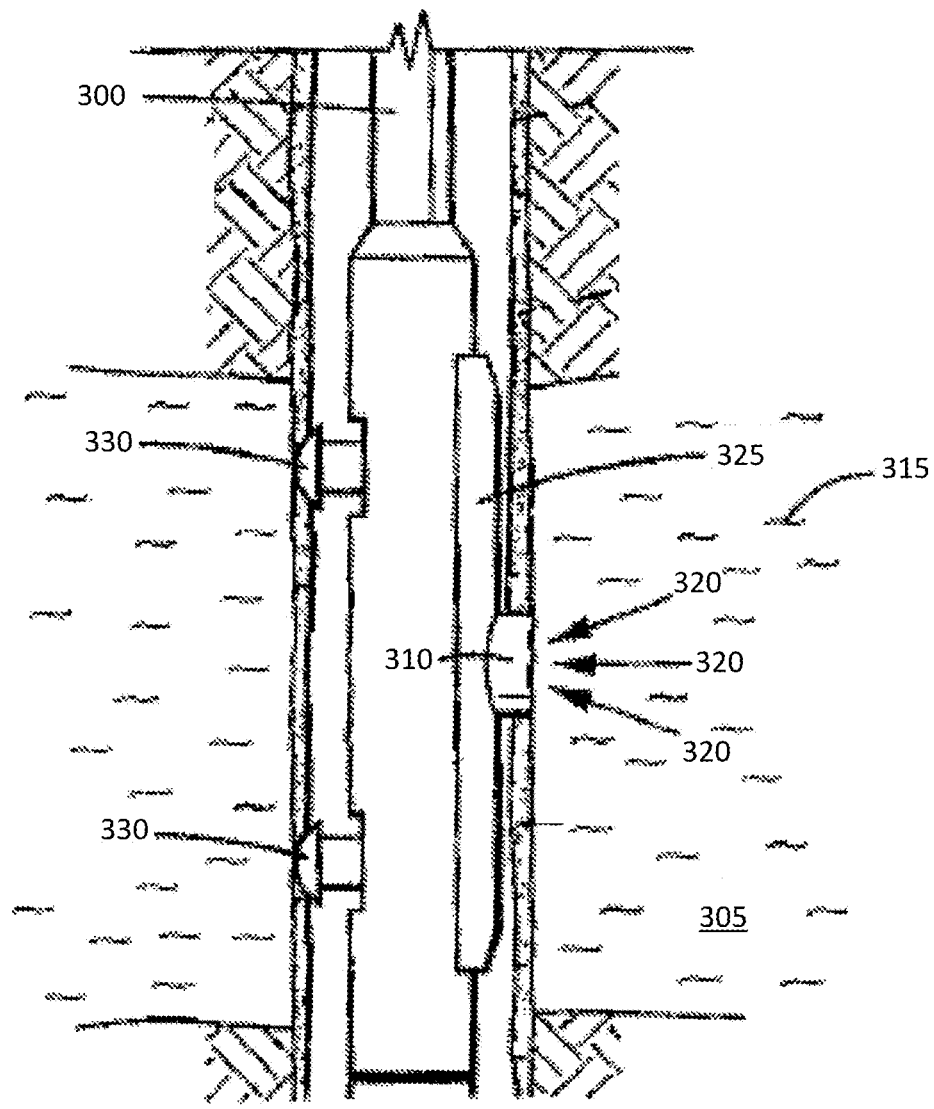
FIG. 3 is a schematic view of apparatus according to one or more aspects of the present disclosure.

An example downhole tool or module 300 that may be utilized in the example systems 100 and 200 of FIGS. 1 and 2, respectively, such as to obtain a static or flowing sample of fluid from a subterranean formation 305 and perform DFA to determine scattering intensity within the obtained fluid sample, is schematically shown in FIG. 3. The tool 300 is provided with a probe 310 for establishing fluid communication with the formation 305 and drawing formation fluid 315 into the tool, as indicated by arrows 320. The probe 310 may be positioned in a stabilizer blade 325 of the tool 300 and extended therefrom to engage the borehole wall. The stabilizer blade 325 may be or comprise one or more blades that are in contact with the borehole wall. Alternatively, or additionally, the tool 300 may comprise backup pistons 330 configured to press the tool 300 and, thus, the probe 310 into contact with the borehole wall. Fluid drawn into the tool 300 via the probe 310 may be measured to determine, for example, pretest and/or pressure parameters. Additionally, the tool 300 may be provided with chambers and/or other devices for collecting fluid samples for retrieval at the surface.

Figure 4:
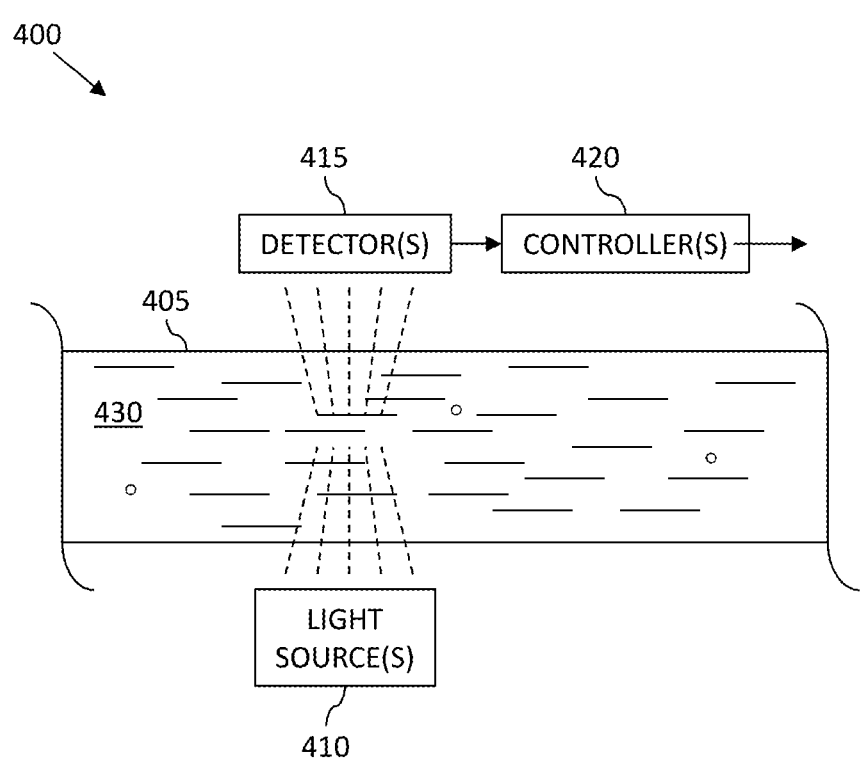
FIG. 4 is a schematic view of apparatus according to one or more aspects of the present disclosure.

An example downhole fluid analyzer 400 that may be used to implement DFA in the example downhole tool 300 shown in FIG. 3 is schematically shown in FIG. 4. The downhole fluid analyzer 400 may be part of or otherwise work in conjunction with a downhole tool configured to obtain a sample of fluid 430 from the formation, such as the downhole tools/modules shown in FIGS. 1-3. For example, a flowline 405 of the downhole tool may extend past an optical spectrometer having one or more light sources 410 and one or more detector(s) 415. Thus, although the example shown in FIG. 4 depicts only one detector 415, other embodiments within the scope of the present disclosure may comprise more than one detector 415, such as where multiple detectors 415 are disposed adjacent or proximate one another along the flowline 405. The detector(s) 415 senses light that has transmitted through the formation fluid 430 in the flowline 405, resulting in optical spectra that may be utilized according to one or more aspects of the present disclosure. For example, one or more controller(s) 420 associated with the downhole fluid analyzer 400 and/or the downhole tool may utilize measured optical spectra to determine or estimate scattering intensity within the formation fluid 430 in the flowline 405 according to one or more aspects of DFA introduced herein. The resulting information may then be reported via any form of telemetry to surface equipment, such as the logging and control unit 190 shown in FIG. 1 or the surface equipment 224 shown in FIG. 2. Moreover, the downhole fluid analyzer 400 may perform the bulk of its processing downhole and report just a relatively small amount of measurement data up to the surface. Thus, the downhole fluid analyzer 400 may provide high-speed (e.g., real time) DFA measurements using a relatively low bandwidth telemetry communication link. As such, the telemetry communication link may be implemented by most types of communication links, unlike conventional DFA techniques that require high-speed communication links to transmit high-bandwidth signals to the surface.

Downhole tools having spectrometers, including those having one or more aspects similar to those described above, may be utilized to determine scattering intensity of a sampled formation fluid according to one or more aspects of the present disclosure. The scattering intensity may then be utilized to determine or estimate dew point, bubble point pressure and/or asphaltene onset pressure of the formation fluid. The dew point, bubble point pressure and/or asphaltene onset pressure may then be utilized in determining whether an operational parameter of the downhole tool requires adjustment. For example, the dew point or bubble point pressure may be utilized to determine an optimum pumping rate during sampling to avoid dropping the pressure below the dew point, bubble point pressure and/or asphaltene onset pressure.

The transmission of light through the fluid sample in the flowline results from the combined effect of two distinct processes—scattering and absorption. Both of these processes affect light transmission and, thereby, the optical density measurements acquired by the downhole spectrometer. These processes also depend on the wavelength of the light. That is, whereas the fluid sample can absorb light of particular wavelengths through both vibrational and electronic excitation, scattering is a non-absorbing process in which the transmitted light interacting with particles and molecules in the fluid are deflected from the path of transmission, thereby reducing optical transmission.

Examples of scattering objects in the flowline may include sand, water droplets, gas bubbles and other particulate material. The intensity of scattering depends on the size of the scattering particles relative to the wavelength of light and the concentration of the scattering particles. When the size of particles is significantly larger than the wavelength, light is simply reflected from the particle surface. In this case, the scattering intensity does not depend on the wavelength of light. In contrast, if the size of the impeding particles is small or comparable to the wavelength of light, then the intensity of scattering can increase with decreasing wavelength. This process, known as Rayleigh scattering, produces wavelength-dependent scattering. The present disclosure introduces methods for detecting the presence of wavelength-dependent and wavelength-independent scattering using, for example, multi-channel optical density measurements obtained by one or more of the apparatus shown in FIGS. 1-4 or otherwise within the scope of the present disclosure, as well as examples of how to use the results in downhole applications.

The wavelength-independent scattering can be represented as a constant offset in the optical density measurement $OD_\lambda$ at the wavelength $\lambda$, as set forth below in Equation (1):

$$OD_\lambda = \overline{OD_\lambda} + \bar{a} \quad (1)$$

where $\overline{OD_\lambda}$ is the optical density measurement at the wavelength $\lambda$ due to the absorption effect, and $\bar{a}$ is the constant offset caused by the wavelength-independent scattering. The offset $\bar{a}$ is constant regardless of which wavelength is considered. For wavelengths ranging between UV and near infrared (e.g., about 400 nm to about 2000 nm) where the downhole spectrometer might operate, the wavelength-dependent scattering can be approximated as a linear function of wavelength. Therefore, including both wavelength-independent scattering and wavelength-dependent scattering, the optical density measurement $OD_\lambda$ at the wavelength $\lambda$ can be approximately written as set forth below in Equation (2):

$$OD_\lambda = \overline{OD_\lambda} + \bar{a} + \bar{b}\lambda^\alpha. \quad (2)$$

where $\bar{b}$ is the coefficient associated with the wavelength-dependent scattering and $\alpha$ is the exponent appropriate to the type of scattering. For example, for Rayleigh scattering, the exponent has a value of −4. In other cases, such as Mie scattering, other exponent values are possible.

With the measured optical density $OD_\lambda$ available, it is unfeasible to obtain the unknown constants $\bar{a}$ and $\bar{b}$ in Equation (2) without knowing $\overline{OD_\lambda}$, the optical density measurement at the wavelength $\lambda$ due to the absorption effect. However, given that the optical density measurements are continuously measured with fluid flowing in the flowline, successive recorded data can be as set forth below in Equation (3):

$$OD_\lambda(t+1) = OD_\lambda(t) + a(t) + b(t)\lambda^\alpha(t) \quad (3)$$

where $OD_\lambda(t+1)$ and $OD_\lambda(t)$ are the optical density measurements at successive time instances, $a(t)$ is the difference of wavelength-independent scattering coefficients at the successive time instances, and $b(t)$ is the difference of wavelength-dependent scattering coefficients at the successive time instances. The time period separating times t and t+1 may range from less than about one second to several seconds, although other times are also within the scope of the present disclosure.

The downhole spectrometer of one or more of the apparatus shown in FIGS. 1-4 or otherwise within the scope of the present disclosure may be a multi-channel spectrometer, and may thus acquire the optical density measurements at multiple wavelength channels. Consequently, the coefficients $a(t)$, $b(t)$ and $\alpha(t)$ may be determined by minimizing the criterion set forth below in Equation (4):

$$\min_{a(t),b(t),\alpha(t)} \Sigma_\lambda |OD_\lambda(t+1) - OD_\lambda(t) - a(t) - b(t)\lambda^\alpha(t)|^p \quad (4)$$

where the summation $\Sigma$ denotes summing over all available wavelength channels. Equation (4) may be solved as the least-squares criterion if the exponent p=2, or as the least-absolute error criterion if the exponent p=1, although other methods are also within the scope of the present disclosure.

Figure 5:
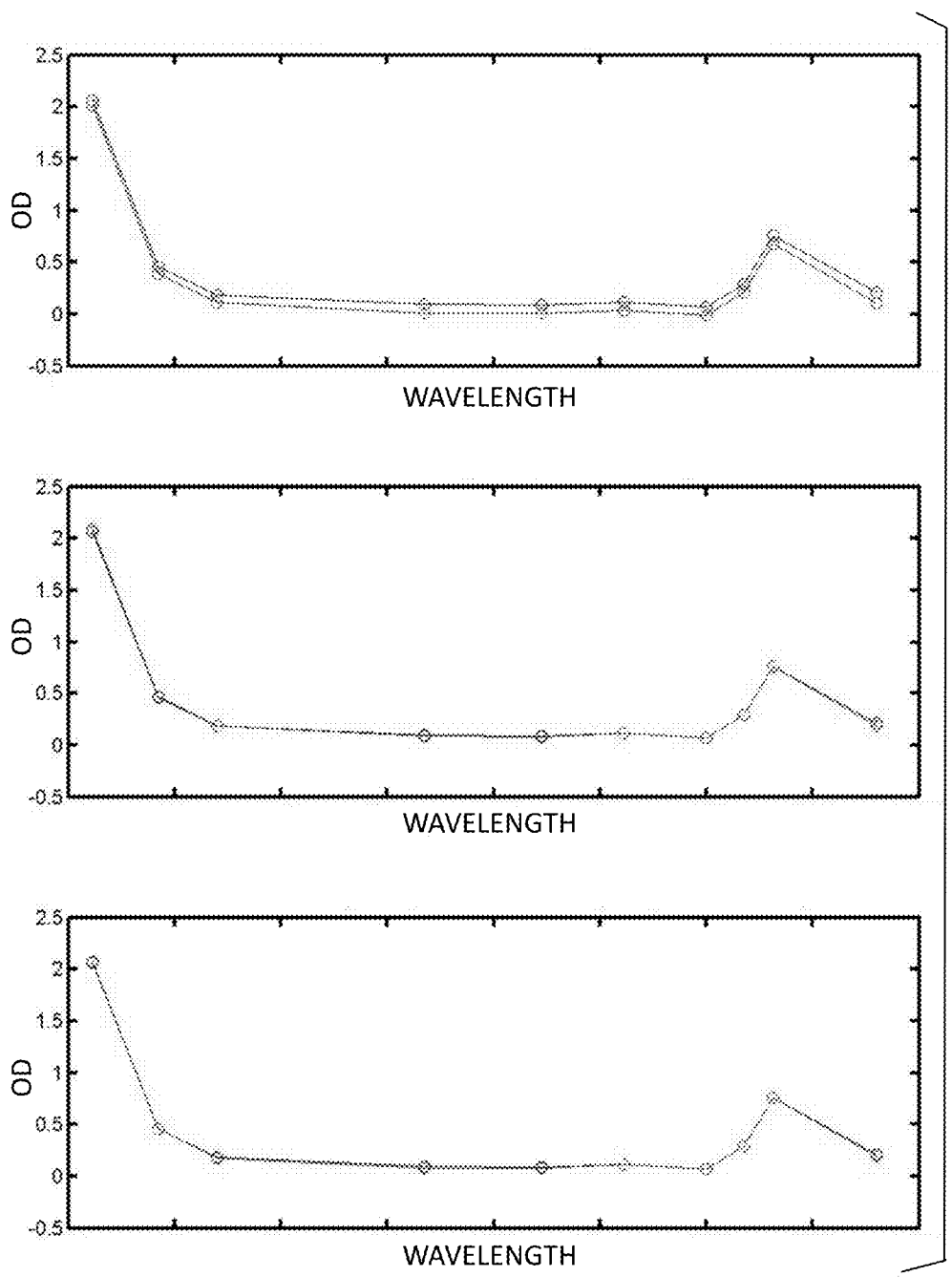
FIG. 5 includes three (3) subplots corresponding to one or more aspects of the present disclosure.

The top subplot of FIG. 5 represents two successive optical density measurements recorded by a multi-channel spectrometer of at least one of FIGS. 1-4 or otherwise within the scope of the present disclosure, with optical density on the Y-axis and wavelength on the X-axis (increasing from left to right on the page). This data is representative of actual field test data with the presence of scattering objects in the flowline. Clearly visible is the offset between the two successive measurements, which conforms to Equation (3) above.

The next (middle) subplot of FIG. 5 depicts the match of the two optical density measurements after the addition of wavelength-independent scattering $a(t)$ to the measured optical density $OD_\lambda(t)$, and the last (bottom) subplot of FIG. 5 depicts the match after the addition of wavelength-independent scattering $a(t)$ and wavelength-dependent scattering $b(t)$ added to the measured optical density $OD_\lambda(t)$. Note that $a(t)$, $b(t)$ and $\alpha(t)$ may be estimated using the least-absolute error criterion of Equation (4), although other estimation methods are also within the scope of the present disclosure. In the example of FIG. 5, the good match in the middle subplot suggests that scattering was dominantly wavelength-independent. This may be corroborated by a substantially small wavelength-dependent scattering coefficient $b(t)$ estimated from the data. For the example presented in FIG. 5, α(t) has a value of 1. Similarly, the value of α(t) in FIGS. 6-10 also has the value of 1. For other data sets, α(t) may a value other than 1, which may be determined according to one or more aspects of the present disclosure.

Figure 6:
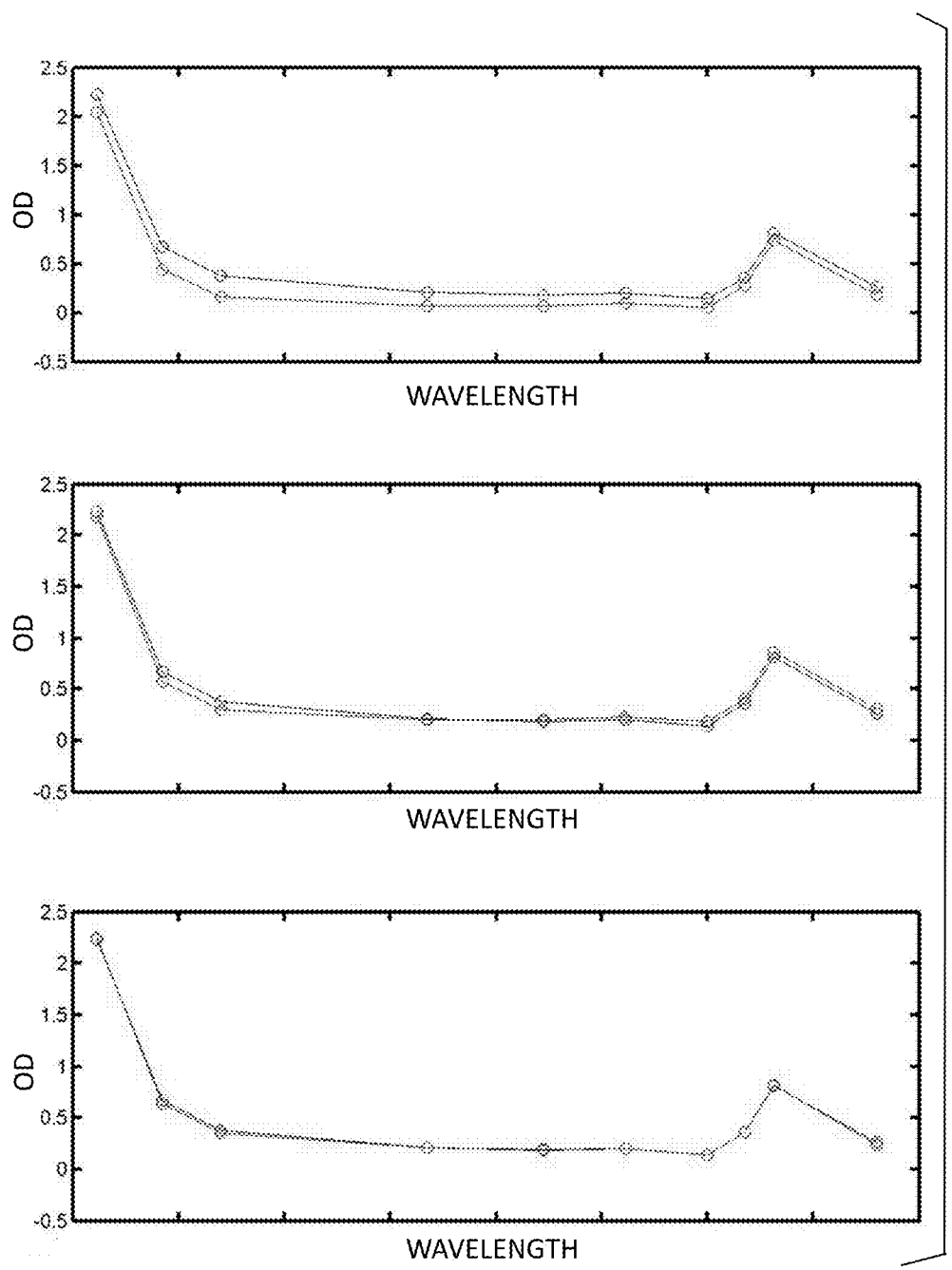
FIG. 6 includes three (3) subplots corresponding to one or more aspects of the present disclosure.

The top subplot of FIG. 6 represents two successive optical density measurements recorded by a multi-channel spectrometer of at least one of FIGS. 1-4 or otherwise within the scope of the present disclosure, with optical density on the Y-axis and wavelength on the X-axis (increasing from left to right on the page). This illustrated data is representative of different field test data with the presence of scattering objects in the flowline. However, in this case, it was insufficient to characterize the scattering as wavelength-independent only from the match of the middle subplot of FIG. 6. After adding the contribution from wavelength-dependent scattering, as depicted in the final (bottom) subplot of FIG. 6, the match of the two plots therein improved, which may indicate that the wavelength-dependent effect was not negligible in this case.

Generally, with scattering objects mixing with sample fluid in the flowline, light scattering would significantly fluctuate from time to time, such that the intensity of scattering (i.e., $\bar{a}$ and $\bar{b}$ in Equation (2) above) would oscillate at the successive time instances. Therefore, obtaining the scattering coefficients a(t) and b(t) may be utilized in the determination of the onset and presence of scattering in the optical density measurements, at least according to one or more aspects of the present disclosure. In contrast, when there are no scattering objects in the flowline, the scattering coefficients a(t) and b(t) may be close to zero.

Alternatively, the semblance of the two successive optical density measurements may be utilized to identify the presence of scattering. The semblance ρ(t) is defined as set forth below in Equation (5):

$$\rho(t) = \frac{\sum_\lambda (OD_\lambda(t+1) + OD_\lambda(t))^2}{2\sum_\lambda (OD_\lambda(t+1)^2 + OD_\lambda(t)^2)} \quad (5)$$

The value of semblance falls between 0 and 1. If ρ(t)=1, it indicates that there is a perfect match between the two successive optical density measurements. With the offset caused by scattering, the semblance would be less than 1. However, with the estimated scattering contributions a(t) and b(t) added to the optical density measurements $OD_\lambda(t)$, the semblance increases and approaches 1.

Figure 7:
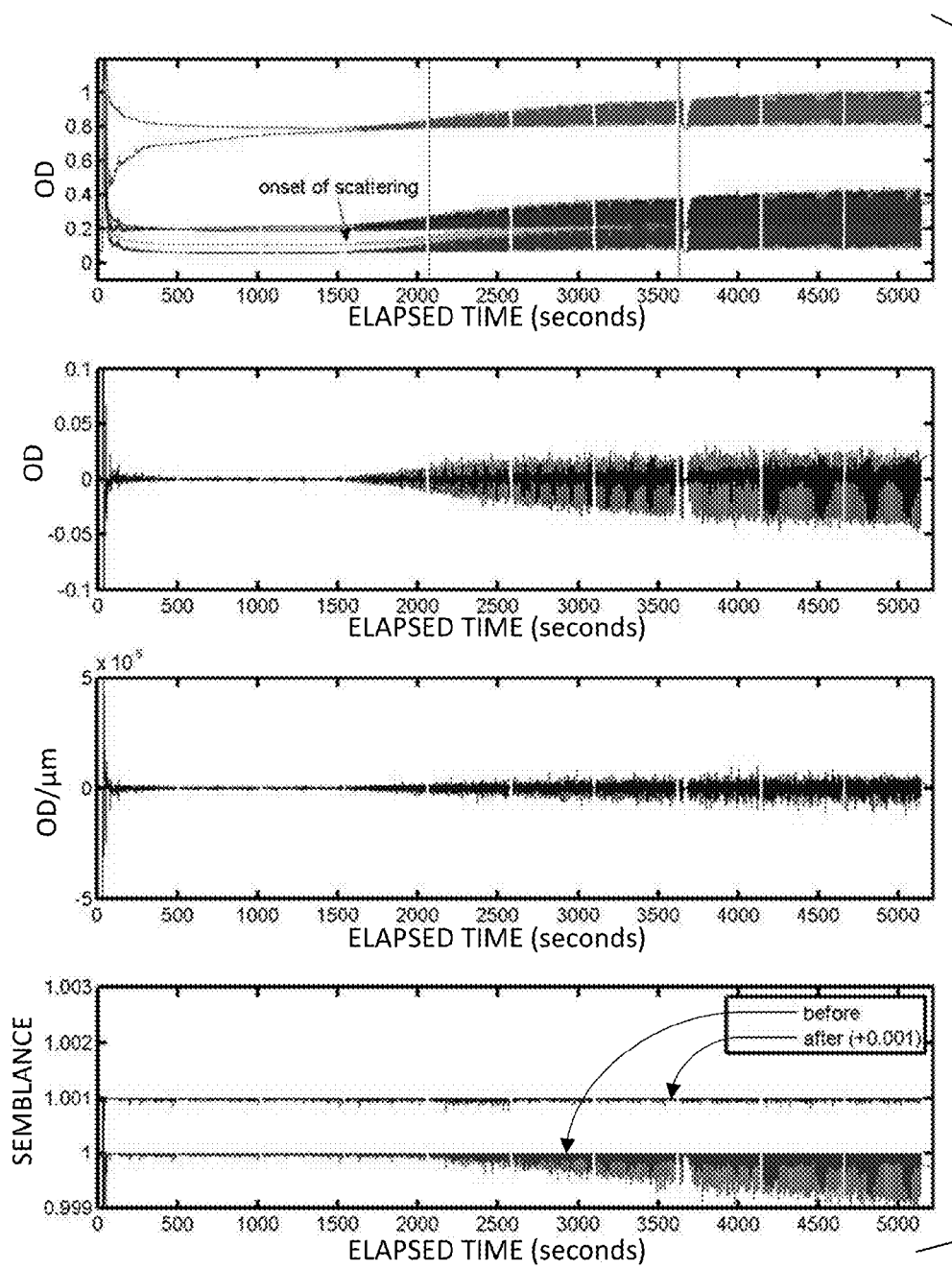
FIG. 7 includes four (4) subplots corresponding to one or more aspects of the present disclosure.

FIG. 7 represents an additional set of multi-channel optical density measurements plotted against the pumping time at an "oil" station in the wellbore, at which the sampled formation fluid was predominantly oil. The second and third subplot of FIG. 7 show the estimated wavelength-independent scattering coefficient a(t) and wavelength-dependent scattering coefficient b(t) obtained by processing successive optical density measurements. The estimated scattering coefficients started showing oscillation at about 1500 seconds, and the magnitude increased gradually thereafter. In this case, the oscillation was caused by the emergence of gas bubbles when the pressure in the flowline dropped below the bubble pressure of the fluid flowing therein. The absence of oscillating features in the early part of testing was caused by a high contamination of oil-based drilling fluid ("mud") filtrate that resulted in a bubble point pressure that was lower than the flowline pressure. While pumping continuously, the filtrate contamination continuously reduced and, as a result, the bubble point pressure of the fluid in the flowline increased. At about 1500 seconds, the bubble point pressure of the fluid in the flowline exceeded the flowline pressure, such that gas bubbles emerged and became scattering objects.

The "before" curve in the fourth subplot of FIG. 7 depicts the semblance resulting from processing successive optical density measurements. The "after" curve represents the semblance processing results obtained from processing successive optical density measurements with the estimated scattering contributions a(t) and b(t) added to the optical density measurements $OD_\lambda(t)$. The "after" curve has been offset in the figure by 0.001 for the purpose of clarity when superimposed with the "before" curve in the same subplot. The semblance was close to 1 in the absence of scattering. By contrast, the semblance decreased after about 1500 seconds, indicating the presence of scattering. However, with the scattering contributions accounted for, the "after" curve depicts the semblance being very close to 1. Thus, in addition to the estimated scattering coefficients, the results of such semblance processing may also be utilized to identify the onset and presence of scattering in the optical density measurements within the scope of the present disclosure.

Figure 8:
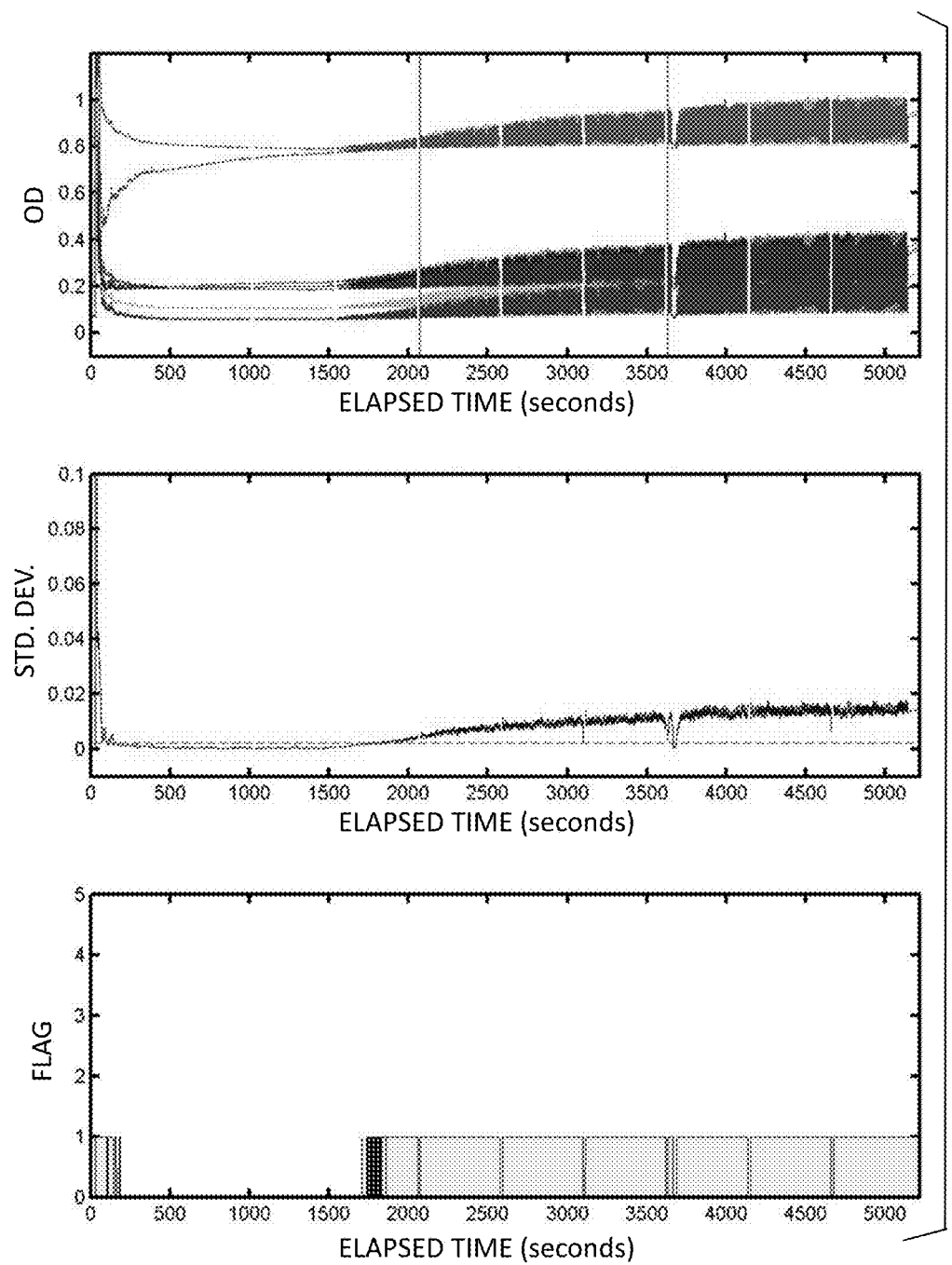
FIG. 8 includes three (3) subplots corresponding to one or more aspects of the present disclosure.

Accordingly, one or more methods introduced herein may comprise monitoring the estimated scattering coefficients and/or the semblance results relative to a corresponding predetermined threshold to detect the presence of scattering in the data. Alternatively, or additionally, one or more methods introduced herein may comprise selecting a running-window and computing the variance (e.g., standard deviation) of the scattering coefficients within the window. The second subplot in FIG. 8 depicts example results of such processing (the first (top) subplot depicts the same multi-channel optical density measurements plotted against the pumping time as shown in FIG. 7). As shown therein, the standard deviation was relatively small in the early time interval where there is no scattering, but increased when gas bubbles emerged. Thus, in the illustrated example of FIG. 8, a predetermined threshold to identify the presence of scattering may have been 0.001, such that when the standard deviation of the scattering coefficients exceeded this predetermined threshold, a scattering flag was triggered, as depicted in the third (bottom) subplot, wherein the shaded region indicates the presence of scattering. Such a scattering flag may be utilized to condense the processing results into one-bit information (0 or 1) to indicate the presence of scattering, which may be advantageous when operations utilize real-time transmission via the mud-telemetry system.

Figure 9:
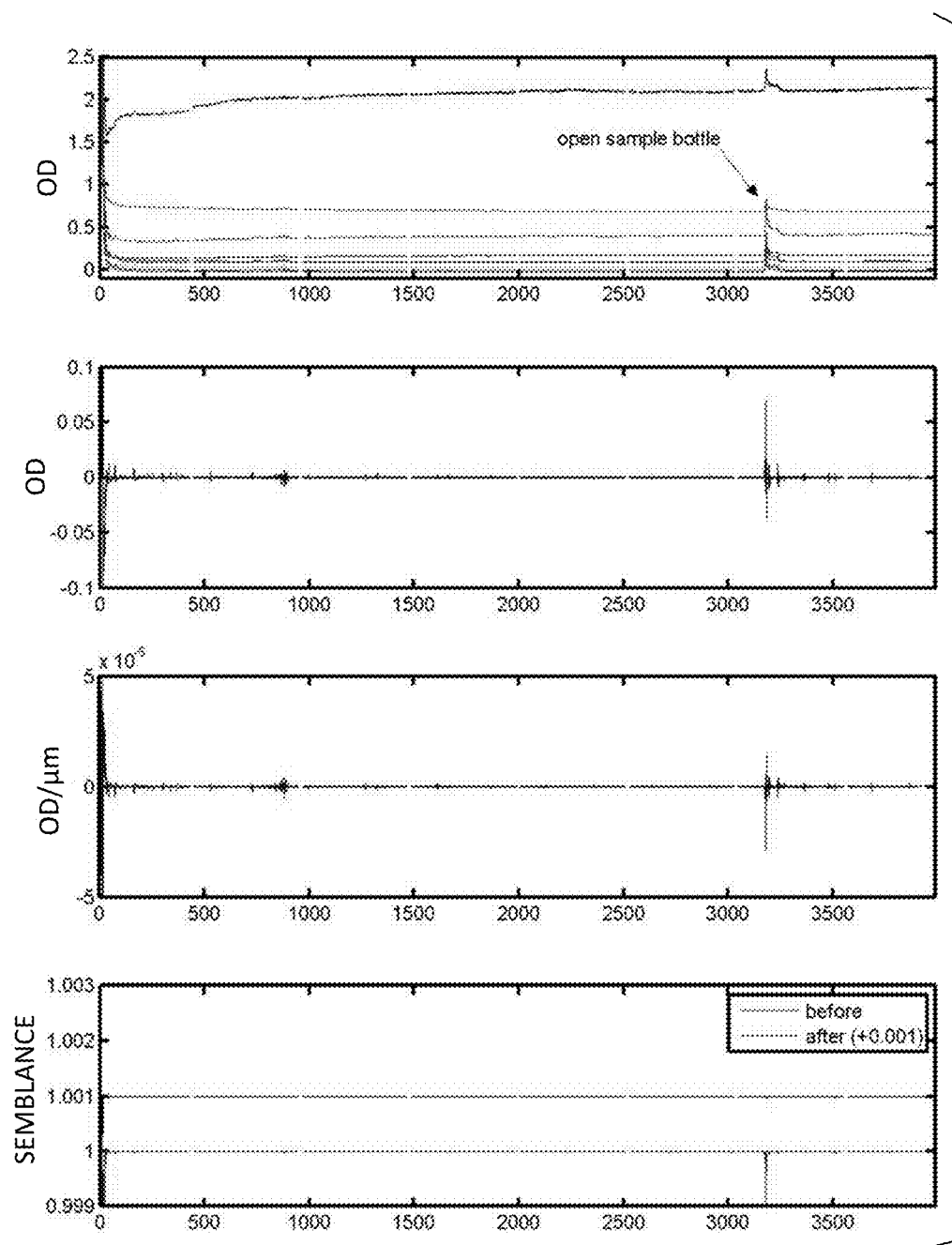
FIG. 9 includes four (4) subplots corresponding to one or more aspects of the present disclosure.
Figure 10:
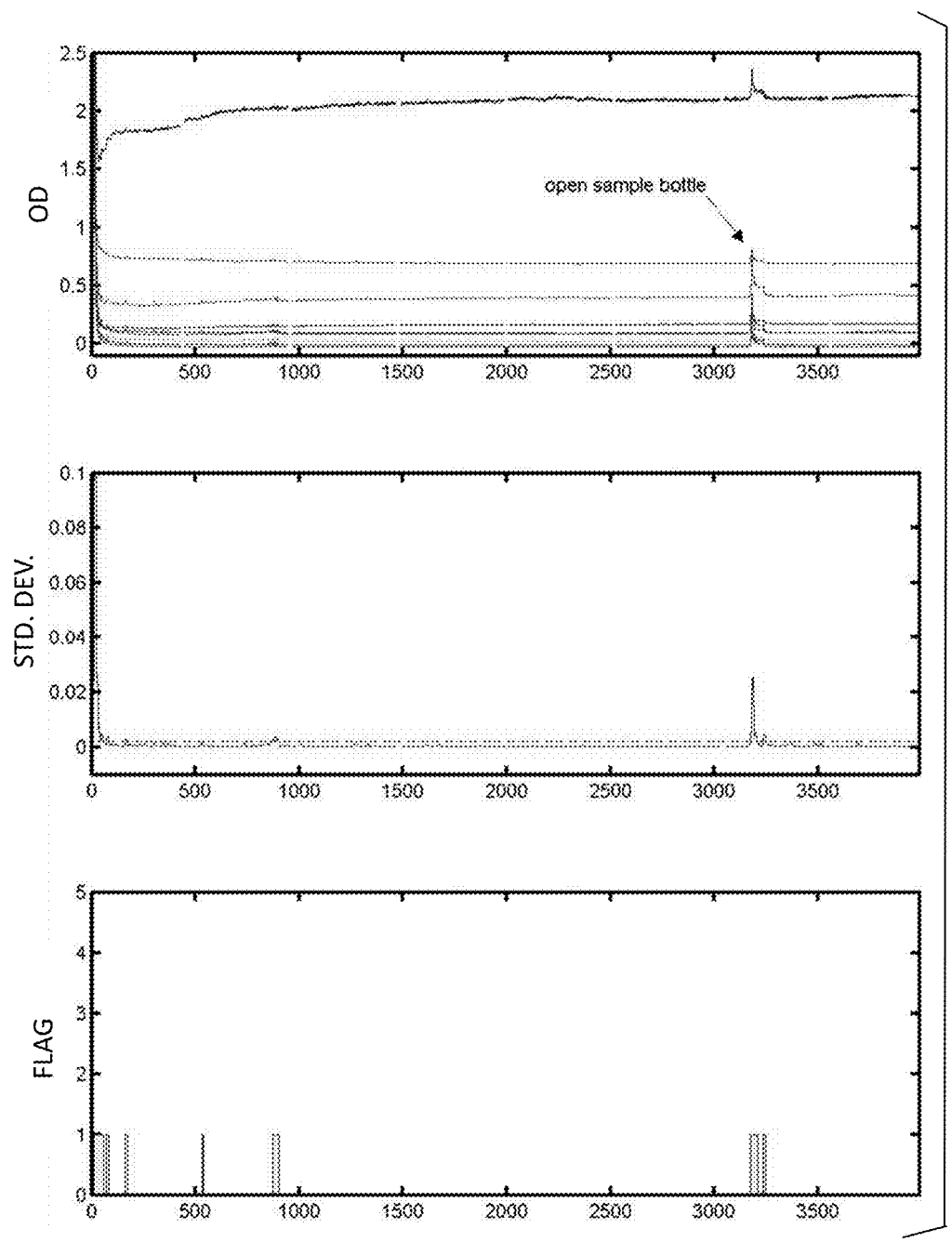
FIG. 10 includes three (3) subplots corresponding to one or more aspects of the present disclosure.

FIGS. 9 and 10 depict another set of multi-channel spectrometer data in an "oil" station and the processing results based on a method within the scope of the present disclosure. Based on the results shown therein, the scattering events were detected sparsely over the entire interval. The data also depicts the results for when the sample bottle was opened at about 3200 seconds.

Figure 11:
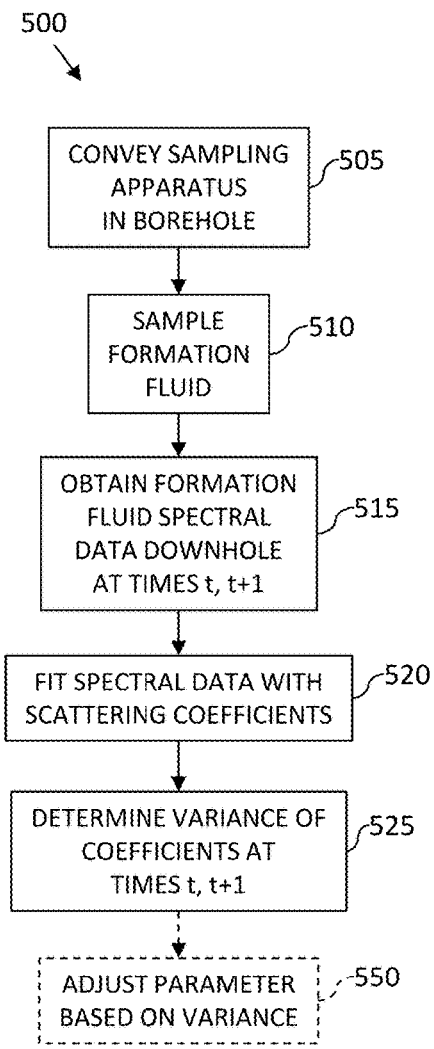
FIG. 11 is a flow-chart diagram of at least a portion of a method according to one or more aspects of the present disclosure.

FIG. 11 is a flow-chart diagram of at least a portion of a method 500 according to one or more aspects of the present disclosure. The method 500 may be at least partially performed by apparatus similar or identical to those shown in the previous figures, described above, or otherwise within the scope of the present disclosure. For example, the method 500 includes a step 505 during which a downhole sampling tool is conveyed along a borehole extending into a subterranean formation, wherein the downhole sampling tool may have one or more aspects in common with the apparatus 170/170A/180 shown in FIG. 1 and/or the apparatus 220 shown in FIG. 2, and may further be part of a BHA having one or more aspects in common with the BHA 150 shown in FIG. 1. The downhole sampling tool may be conveyed via wireline, one or more strings of tubulars (including drill-string and/or wired drill pipe), and/or other means. Once reaching the desired subterranean formation or station within the borehole, the downhole sampling tool obtains formation fluid from the formation during a step 510.

The sampled formation fluid is then subjected to in-situ downhole analysis via a spectrometer of the downhole sampling tool during a step 515, thereby obtaining spectral data representative of the sampled formation fluid at successive times (e.g., t and t+1). Such spectral data associated with the formation fluid flowing through the flowline of the downhole sampling tool may be obtained, at least in part, via a multi-channel optical sensor of the downhole sampling tool, such as the optical detector 415 and/or a larger portion or all of the downhole fluid analyzer 400, each shown in FIG. 4 and described above. In implementations utilizing multiple detectors and/or spectrometers, step 515 may comprise utilizing a first detector and/or spectrometer to obtain spectral data at time t and utilizing a second detector and/or spectrometer to obtain spectral data at time t+1. The sensor (s), detector(s), spectrometer(s) and/or analyzer(s) utilized to obtain the spectral data during step 515 may be or comprise a 20-channel spectrometer, although spectrometers utilizing more or less than 20 channels are also within the scope of the present disclosure. Obtaining the spectral data during step 515 may also be performed while the downhole sampling tool (also interchangeably referred to herein as a downhole formation fluid sampling apparatus) pumps formation fluid from the formation downhole and through the flowline of the downhole sampling tool. However, one or more aspects of the present disclosure may be applicable or readily adaptable to the spectral data being obtained utilizing a static sample of formation fluid captured in a chamber of the downhole sampling tool.

Although not shown in FIG. 11, the method 500 (as well as other methods within the scope of the present disclosure) may also comprise one or more optional steps during which the measured optical spectra may be adjusted prior to continuing with the method 500. For example, water spectra may be removed from the measured optical spectra and/or the measured optical spectra may be de-colored. Other adjustments and/or pre-processing made to the spectral data are also within the scope of the present disclosure.

In a subsequent step 520, the spectral data may be fit with scattering coefficients as described above. That is, the spectral data obtained at times t and t+1 may be fit with a wavelength-independent scattering coefficient a(t) and a wavelength-dependent scattering coefficient b(t). Such analysis may be performed by the downhole sampling tool and/or surface equipment. For example, such analysis may be performed automatically by the downhole sampling tool in response to any number of potential triggers including, for example, fluid flow through the flowline of the downhole sampling tool.

The method 500 then continues to a step 525 during which the variance of the scattering coefficients at times t and t+1 are determined. As with the fitting of the scattering coefficients performed during step 520, the variance of the scattering coefficients may be performed by the downhole tool and/or surface equipment, and the downhole sampling tool may automatically perform such analysis in response to completion of the fitting step 520 and/or some other trigger.

The method 500 may also comprise an optional step 550 during which one or more operating parameters of the downhole sampling tool may be adjusted based on the scattering coefficient variance determined during step 525. For example, if the determined variance of the scattering coefficients exceeds a predetermined threshold or otherwise indicates an undesirable intensity of scattering, as described above, the rate and/or output pressure of a pump of the downhole sampling tool may be adjusted. Such adjustment may reduce the intensity of scattering within the fluid flowing through the flowline of the downhole sampling tool, such as by increasing the pressure above the dew point or bubble point pressure of the fluid flowing in the flowline. Moreover, the adjustment may be in proportion to the determined scattering intensity, and perhaps in proportion to the magnitude or other extent by which the predetermined threshold is exceeded.

Figure 12:
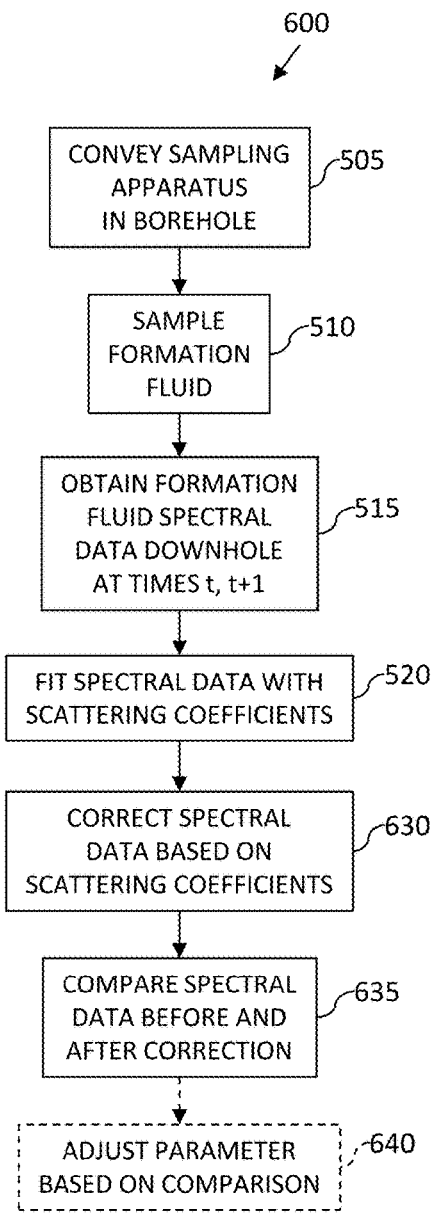
FIG. 12 is a flow-chart diagram of at least a portion of a method according to one or more aspects of the present disclosure.

FIG. 12 is a flow-chart diagram of at least a portion of a method 600 according to one or more aspects of the present disclosure. The method 600 may be at least partially performed by apparatus similar or identical to those shown in the previous figures, described above, or otherwise within the scope of the present disclosure. Moreover, aspects of the method 600 are similar or identical to those of the method 500 shown in FIG. 11 and described above. For example, the repeat of reference numerals and/or letters in FIGS. 11 and 12 indicates aspects of FIGS. 11 and 12 that are similar or identical. Accordingly, the method 600 comprises steps 505, 510, 515 and 520, which are described in detail above with respect to the method 500 shown in FIG. 11. However, the method 600 shown in FIG. 12 also comprises steps 630 and 635, and perhaps optional step 640.

During step 630, the measured spectral data is corrected based on the scattering coefficients fit during previous step 520. For example, the offsets in measured optical density may be reduced or substantially eliminated by adjusting the measured spectral data utilizing the scattering coefficients. Thereafter, during subsequent step 635, the corrected and uncorrected spectral measurements may be compared, perhaps in the manner described above with respect to determining the semblance of the corrected and uncorrected spectral measurements. During optional step 640, one or more operating parameters of the downhole sampling tool may be adjusted based on the semblance/comparison of the corrected and uncorrected spectral data determined during step 635. For example, if the determined semblance/comparison of the corrected and uncorrected spectral data exceeds a predetermined threshold or otherwise indicates an undesirable intensity of scattering, as described above, the rate and/or output pressure of a pump of the downhole sampling tool may be adjusted. Such adjustment may reduce the intensity of scattering within the fluid flowing through the flowline of the downhole sampling tool, such as by increasing the pressure above the dew point or bubble point pressure of the fluid flowing in the flowline. Moreover, the adjustment may be in proportion to the determined scattering intensity, and perhaps in proportion to the magnitude or other extent by which the predetermined threshold is exceeded.

Figure 13:
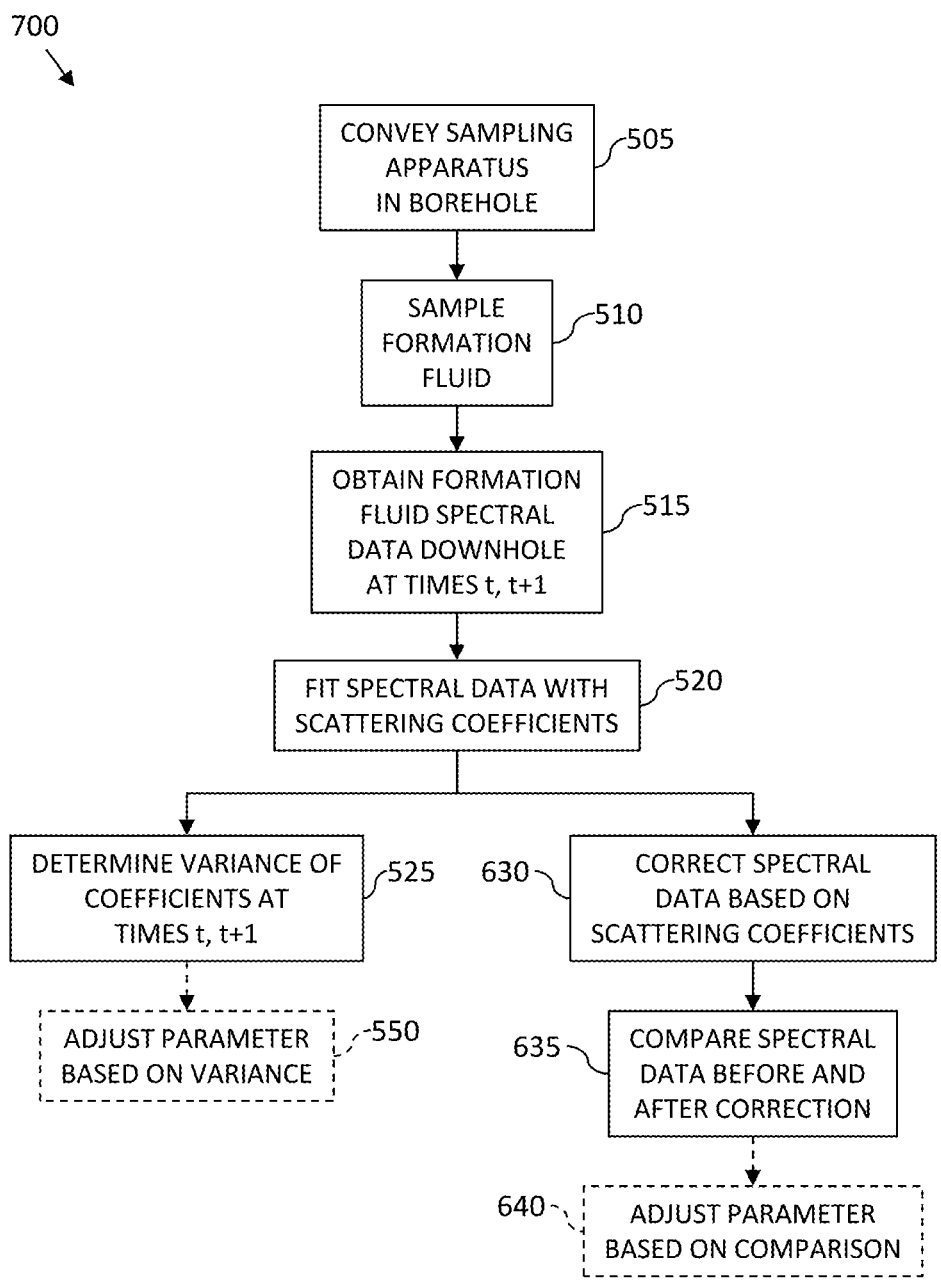
FIG. 13 is a flow-chart diagram of at least a portion of a method according to one or more aspects of the present disclosure.

FIG. 13 is a flow-chart diagram of at least a portion of a method 700 according to one or more aspects of the present disclosure. The method 700 may be at least partially performed by apparatus similar or identical to those shown in the previous figures, described above, or otherwise within the scope of the present disclosure. Moreover, aspects of the method 700 are similar or identical to those described above with respect to the method 500 shown in FIG. 11 and/or the method 600 shown in FIG. 12. For example, the repeat of reference numerals and/or letters in FIGS. 11-13 indicates aspects of FIGS. 11-13 that are similar or identical. Accordingly, the method 600 comprises steps 505, 510, 515 and 520, which are described in detail above with respect to the method 500 shown in FIG. 11. However, the method 700 shown in FIG. 13 also comprises step 525 of the method 500 shown in FIG. 11 or the steps 630 and 635 of the method 600 shown in FIG. 12, and perhaps the optional step 550 of the method 500 and/or the optional step 640 of the method 600.

That is, the method 700 incorporates the option to determine scattering intensity either by determining the variance of the scattering coefficients, as in the step 525 of the method 500, or by determining the semblance of the corrected and uncorrected spectral data, as in the step 635 of the method 600. If, during a particular iteration of the method 700, the scattering coefficient variance exceeds a predetermined threshold or otherwise indicates an undesirable intensity of scattering within the fluid in the flowline of the downhole sampling tool, then an operating parameter of the downhole sampling tool may be adjusted during the step 550, perhaps in proportion to or otherwise based on the magnitude or other extent by which the predetermined threshold is exceeded. Alternatively, if the semblance of the corrected and uncorrected spectral data exceeds a predetermined threshold or otherwise indicates an undesirable intensity of scattering, then an operating parameter of the downhole sampling tool may be adjusted during the step 640, perhaps based on the magnitude or other extent by which the predetermined threshold is exceeded.

Figure 14:
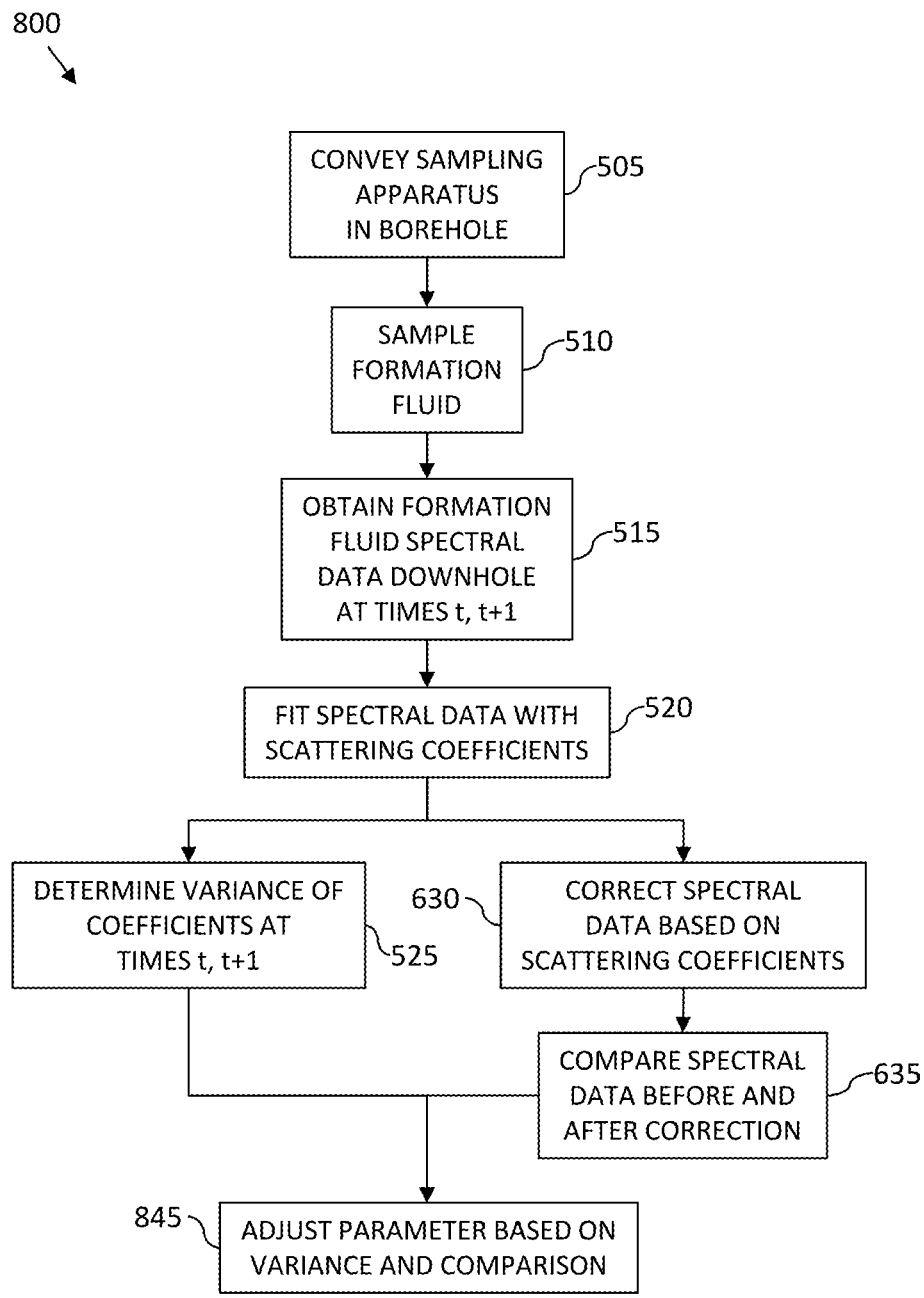
FIG. 14 is a flow-chart diagram of at least a portion of a method according to one or more aspects of the present disclosure.

FIG. 14 is a flow-chart diagram of at least a portion of a method 800 according to one or more aspects of the present disclosure. The method 800 may be at least partially performed by apparatus similar or identical to those shown in the previous figures, described above, or otherwise within the scope of the present disclosure. Moreover, aspects of the method 800 are similar or identical to those described above with respect to the method 500 shown in FIG. 11 and/or the method 600 shown in FIG. 12. For example, the repeat of reference numerals and/or letters in FIGS. 11, 12 and 14 indicates aspects of FIGS. 11, 12 and 14 that are similar or identical. Accordingly, the method 800 comprises steps 505, 510, 515 and 520, which are described in detail above with respect to the method 500 shown in FIG. 11. The method 800 also comprises step 525 of the method 500 shown in FIG. 11, the steps 630 and 635 of the method 600 shown in FIG. 12, and a step 845.

That is, the method 800 comprises determining scattering intensity by determining the variance of the scattering coefficients, as in the step 525 of the method 500, and by determining the semblance of the corrected and uncorrected spectral data, as in the step 635 of the method 600. Thereafter, during step 845, an operating parameter of the downhole sampling tool is adjusted based on both the scattering coefficient variance and the semblance of the corrected and uncorrected spectral data. For example, during a particular iteration of the method 800, if the scattering coefficient variance indicates an undesirable intensity of scattering within the fluid in the flowline of the downhole sampling tool, and the semblance of the corrected and uncorrected spectral data also indicates an undesirable intensity of scattering, then an operating parameter of the downhole sampling tool may be adjusted during the step 845. In contrast, if either the scattering coefficient variance or the semblance of the corrected and uncorrected spectral data fails to indicate an undesirable intensity of scattering, even if the other one does indicate undesirable scattering, then the parameter adjustment of step 845 may be omitted.

In each of the methods shown in the figures, described above, or otherwise within the scope of the present disclosure, there may exist additional applications for utilizing the detection of scattering or scattering intensity. For example, known examples of scattering objects in the flowline such as gas bubbles, precipitated asphaltene and/or others may be caused by the drawdown pressure in the flowline falling below a saturation pressure (e.g., bubble point pressure, asphaltene onset pressure, etc.). Thus, aspects of one or more methods within the scope of the present disclosure may allow the manual or automatic control of the pump of the downhole sampling tool, such that the drawdown pressure may be maintained at or above the saturation pressures.

Moreover, as described above, the wavelength-dependent and wavelength-independent scattering coefficients are related to the size of scattering objects. Therefore, at least according to one or more aspects of the present disclosure, the coefficients may be also or alternatively be used to identify the size of the scattering objects flowing within the flowline.

Detection of scattering or scattering intensity according to aspects of the present disclosure may also or alternatively be utilized as quality control measures for various optical density measurements and answer products derived from the optical density measurements. Examples of such measurements and/or answer products may include composition and/or gas-oil-ratio (GOR) of the fluid flowing through the flowline of the downhole sampling tool, although quality control measures for other measurements and/or answer products are also within the scope of the present disclosure.

Additionally, because the above-described process for determining scattering intensity depends on the variance and/or semblance related to the scattering coefficients, the process may be more robust than previous methods and apparatus utilized for scattering detection. For example, in embodiments within the scope of the present disclosure in which the scattering or scattering intensity is determined utilizing multiple optical density measurements in close succession, the effect of debris and/or other contaminants on the spectrometer optics (e.g., lenses) may be reduced, if not eliminated altogether. Nonetheless, some embodiments within the scope of the present disclosure may still require appropriate treatment or adaptation if the spectrometer optics become contaminated.

Figure 15:
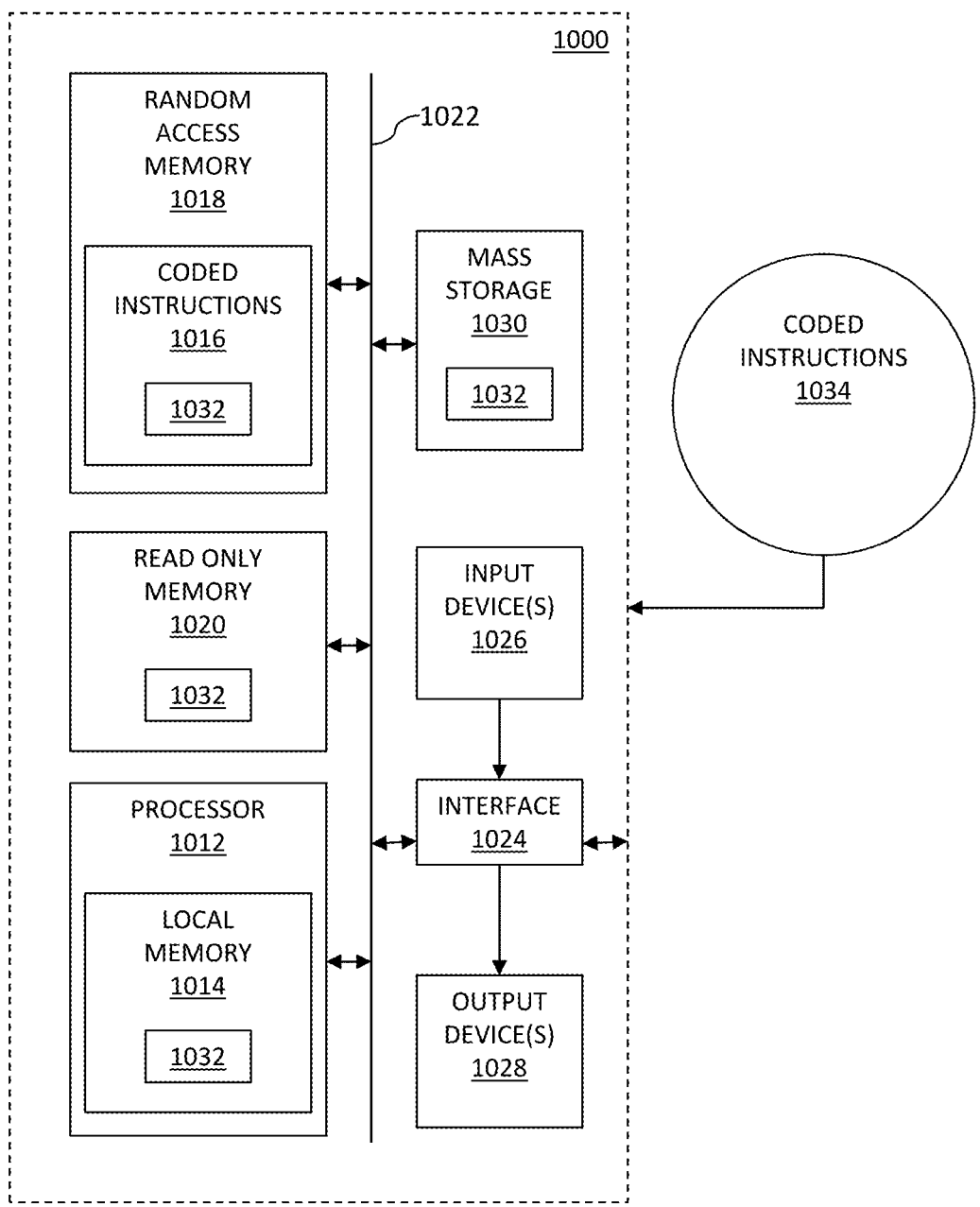
FIG. 15 is a schematic view of apparatus according to one or more aspects of the present disclosure.

FIG. 15 is a block diagram of an example processing system 1000 that may execute example machine-readable instructions used to implement one or more of the processes of FIGS. 11-14, and/or to implement the example downhole fluid analyzers and/or other apparatus of FIGS. 1-4. Thus, the example processing system 1000 may be capable of implementing the apparatus and methods disclosed herein. The processing system 1000 may be or comprise, for example, one or more processors, one or more controllers, one or more special-purpose computing devices, one or more servers, one or more personal computers, one or more personal digital assistant (PDA) devices, one or more smartphones, one or more internet appliances, and/or any other type(s) of computing device(s). Moreover, while it is possible that the entirety of the system 1000 shown in FIG. 15 is implemented within the downhole tool, it is also contemplated that one or more components or functions of the system 1000 may be implemented in surface equipment, such as the surface equipment 190 shown in FIG. 1, and/or the surface equipment 224 shown in FIG. 2. One or more aspects, components or functions of the system 1000 may also or alternatively be implemented as the controller 420 shown in FIG. 4.

The system 1000 comprises a processor 1012 such as, for example, a general-purpose programmable processor. The processor 1012 includes a local memory 1014, and executes coded instructions 1032 present in the local memory 1014 and/or in another memory device. The processor 1012 may execute, among other things, machine readable instructions to implement the processes represented in FIGS. 11-14. The processor 1012 may be, comprise or be implemented by any type of processing unit, such as one or more INTEL microprocessors, one or more microcontrollers from the ARM and/or PICO families of microcontrollers, one or more embedded soft/hard processors in one or more FPGAs, etc. Of course, other processors from other families are also appropriate.

The processor 1012 is in communication with a main memory including a volatile (e.g., random access) memory 1018 and a non-volatile (e.g., read only) memory 1020 via a bus 1022. The volatile memory 1018 may be, comprise or be implemented by static random access memory (SRAM), synchronous dynamic random access memory (SDRAM), dynamic random access memory (DRAM), RAMBUS dynamic random access memory (RDRAM) and/or any other type of random access memory device. The non-volatile memory 1020 may be, comprise or be implemented by flash memory and/or any other desired type of memory device. One or more memory controllers (not shown) may control access to the main memory 1018 and/or 1020.

The processing system 1000 also includes an interface circuit 1024. The interface circuit 1024 may be, comprise or be implemented by any type of interface standard, such as an Ethernet interface, a universal serial bus (USB) and/or a third generation input/output (3GIO) interface, among others.

One or more input devices 1026 are connected to the interface circuit 1024. The input device(s) 1026 permit a user to enter data and commands into the processor 1012. The input device(s) may be, comprise or be implemented by, for example, a keyboard, a mouse, a touchscreen, a trackpad, a trackball, an isopoint and/or a voice recognition system, among others.

One or more output devices 1028 are also connected to the interface circuit 1024. The output devices 1028 may be, comprise or be implemented by, for example, display devices (e.g., a liquid crystal display or cathode ray tube display (CRT), among others), printers and/or speakers, among others. Thus, the interface circuit 1024 may also comprise a graphics driver card.

The interface circuit 1024 also includes a communication device such as a modem or network interface card to facilitate exchange of data with external computers via a network (e.g., Ethernet connection, digital subscriber line (DSL), telephone line, coaxial cable, cellular telephone system, satellite, etc.).

The processing system 1000 also includes one or more mass storage devices 1030 for storing machine-readable instructions and data. Examples of such mass storage devices 1030 include floppy disk drives, hard drive disks, compact disk drives and digital versatile disk (DVD) drives, among others.

The coded instructions 1032 may be stored in the mass storage device 1030, the volatile memory 1018, the non-volatile memory 1020, the local memory 1014 and/or on a removable storage medium, such as a CD or DVD 1034.

As an alternative to implementing the methods and/or apparatus described herein in a system such as the processing system of FIG. 15, the methods and or apparatus described herein may be embedded in a structure such as a processor and/or an ASIC (application specific integrated circuit).

In view of all of the above and the figures, those having ordinary skill in the art should readily recognize that the present disclosure introduces a method comprising: obtaining in-situ, at a first time, first optical spectral data associated with a formation fluid flowing through a downhole formation fluid sampling apparatus; obtaining in-situ, at a second time after the first time, second optical spectral data associated with the formation fluid flowing through the downhole formation fluid sampling apparatus; determining a wavelength-independent scattering intensity within the formation fluid flowing through the downhole formation fluid sampling apparatus based on the first and second optical spectral data; and determining a wavelength-dependent scattering intensity within the formation fluid flowing through the downhole formation fluid sampling apparatus based on the first and second optical spectral data. Such method may further comprise adjusting an operating parameter associated with the downhole formation fluid sampling apparatus based on at least one of the determined wavelength-independent scattering intensity and the determined wavelength-dependent scattering intensity. The operating parameter may be an operating parameter of a pump of the downhole formation fluid sampling apparatus. Adjusting the operating parameter of the pump may comprise decreasing a flow-rate of the pump based on at least one of the determined wavelength-independent scattering intensity and the determined wavelength-dependent scattering intensity. Determining the wavelength-independent scattering intensity and the wavelength-dependent scattering intensity within the formation fluid flowing through the downhole formation fluid sampling apparatus may comprise fitting the first and second optical spectral data with a wavelength-independent scattering coefficient and a wavelength-dependent scattering coefficient. Determining the wavelength-independent scattering intensity may comprise determining a variance of the wavelength-independent scattering coefficient in real-time, and determining the wavelength-dependent scattering intensity may comprise determining a variance of the wavelength-dependent scattering coefficient in real-time. Determining the wavelength-independent scattering intensity may comprise detecting when the variance of the wavelength-independent scattering coefficient exceeds a first predetermined threshold, and determining the wavelength-dependent scattering intensity may comprise detecting when the variance of the wavelength-dependent scattering coefficient exceeds a second predetermined threshold. Determining the wavelength-independent scattering intensity and the wavelength-dependent scattering intensity may comprise determining in real-time a semblance of the first and second optical spectral data before and after correcting the first and second optical spectral data based on the determined wavelength-independent scattering coefficient and the determined wavelength-dependent scattering coefficient. The first and second optical spectral data may be obtained at least in part via a multi-channel optical sensor of the downhole formation fluid sampling apparatus, and the multi-channel optical sensor of the downhole formation fluid sampling apparatus may comprise at least one spectrometer. The method may further comprise conveying the downhole formation fluid sampling apparatus within a wellbore extending into the formation, wherein the conveying may be via at least one of wireline and a string of tubulars. The method may further comprise estimating a gas-to-oil ratio (GOR) of the formation fluid flowing through the downhole formation fluid sampling apparatus based on at least one of the determined wavelength-independent scattering intensity and the determined wavelength-dependent scattering intensity. Such estimate may be utilized as quality control for the estimated GOR and/or composition.

The present disclosure also introduces a system comprising: means for obtaining in-situ: first optical spectral data associated with a formation fluid flowing through a downhole formation fluid sampling apparatus at a first time; and second optical spectral data associated with the formation fluid flowing through the downhole formation fluid sampling apparatus at a second time; and means for determining: a wavelength-independent scattering intensity within the formation fluid flowing through the downhole formation fluid sampling apparatus based on the first and second optical spectral data; and a wavelength-dependent scattering intensity within the formation fluid flowing through the downhole formation fluid sampling apparatus based on the first and second optical spectral data. Such system may further comprise means for automatically adjusting an operating parameter associated with the downhole formation fluid sampling apparatus based on at least one of the determined wavelength-independent scattering intensity and the determined wavelength-dependent scattering intensity, wherein the adjusting means and the determining means may be communicably coupled. The operating parameter may be an operating parameter of a pump of the downhole formation fluid sampling apparatus. The means for automatically adjusting the operating parameter of the pump may comprise means for automatically decreasing a flow-rate of the pump based on at least one of the determined wavelength-independent scattering intensity and the determined wavelength-dependent scattering intensity. The determining means may comprise means for fitting the first and second optical spectral data with a wavelength-independent scattering coefficient and a wavelength-dependent scattering coefficient. The determining means may comprise means for determining a variance of the wavelength-independent scattering coefficient and the wavelength-dependent scattering coefficient in real-time. The determining means may comprise means for detecting at least one of: the variance of the wavelength-independent scattering coefficient exceeding a first predetermined threshold; and the variance of the wavelength-dependent scattering coefficient exceeding a second predetermined threshold. The determining means may comprise means for determining in real-time a semblance of the first and second optical spectral data before and after correcting the first and second optical spectral data based on the determined wavelength-independent scattering coefficient and the determined wavelength-dependent scattering coefficient. The obtaining means may comprise a multi-channel optical sensor of the downhole formation fluid sampling apparatus, and the multi-channel optical sensor of the downhole formation fluid sampling apparatus may comprise at least one spectrometer. The system may further comprise means for conveying the downhole formation fluid sampling apparatus within a wellbore extending into the formation, wherein the conveying means may comprise at least one of a wireline and a string of tubulars. The system may further comprise means for estimating a gas-to-oil ratio (GOR) of the formation fluid flowing through the downhole formation fluid sampling apparatus based on at least one of the determined wavelength-independent scattering intensity and the determined wavelength-dependent scattering intensity. Such estimate may be utilized as quality control for the estimated GOR and/or composition.

The present disclosure also introduces a method comprising: obtaining in-situ, at a first time, first optical spectral data associated with a formation fluid flowing through a downhole formation fluid sampling apparatus; obtaining in-situ, at a second time after the first time, second optical spectral data associated with the formation fluid flowing through the downhole formation fluid sampling apparatus; determining a wavelength-independent scattering intensity within the formation fluid flowing through the downhole formation fluid sampling apparatus based on the first and second optical spectral data; and determining a wavelength-dependent scattering intensity within the formation fluid flowing through the downhole formation fluid sampling apparatus based on the first and second optical spectral data. The method may further comprise adjusting an operating parameter associated with the downhole formation fluid sampling apparatus based on at least one of the determined wavelength-independent scattering intensity and the determined wavelength-dependent scattering intensity. The operating parameter may be an operating parameter of a pump of the downhole formation fluid sampling apparatus. Adjusting the operating parameter of the pump may comprise decreasing a flow-rate of the pump based on at least one of the determined wavelength-independent scattering intensity and the determined wavelength-dependent scattering intensity.

Determining the wavelength-independent scattering intensity and the wavelength-dependent scattering intensity within the formation fluid flowing through the downhole formation fluid sampling apparatus may comprise fitting the first and second optical spectral data with a wavelength-independent scattering coefficient and a wavelength-dependent scattering coefficient. Determining the wavelength-independent scattering intensity may comprise determining a variance of the wavelength-independent scattering coefficient in real-time, and determining the wavelength-dependent scattering intensity may comprise determining a variance of the wavelength-dependent scattering coefficient in real-time. Determining the wavelength-independent scattering intensity may comprise detecting when the variance of the wavelength-independent scattering coefficient exceeds a first predetermined threshold, and determining the wavelength-dependent scattering intensity may comprise detecting when the variance of the wavelength-dependent scattering coefficient exceeds a second predetermined threshold. Determining the wavelength-independent scattering intensity and the wavelength-dependent scattering intensity may comprise determining in real-time a semblance of the first and second optical spectral data before and after correcting the first and second optical spectral data based on the determined wavelength-independent scattering coefficient and the determined wavelength-dependent scattering coefficient.

The first and second optical spectral data may be obtained at least in part via a multi-channel optical sensor of the downhole formation fluid sampling apparatus, and the multi-channel optical sensor of the downhole formation fluid sampling apparatus may comprise at least one spectrometer. The downhole formation fluid sampling apparatus may comprise a first spectrometer and a second spectrometer, wherein obtaining the first optical spectral data may utilize the first spectrometer, and wherein obtaining the second optical spectral data may utilize the second spectrometer.

The method may further comprise assessing the quality of at least one answer product based on at least one of the determined wavelength-independent scattering intensity and the determined wavelength-dependent scattering intensity. Assessing the quality of at least one answer product may comprise estimating a gas-to-oil ratio (GOR) of the formation fluid flowing through the downhole formation fluid sampling apparatus based on at least one of the determined wavelength-independent scattering intensity and the determined wavelength-dependent scattering intensity.

The method may further comprise identifying the size of scattering objects flowing within the downhole formation fluid sampling apparatus based on at least one of the determined wavelength-independent scattering intensity and the determined wavelength-dependent scattering intensity.

The method may further comprise conveying the downhole formation fluid sampling apparatus within a wellbore extending into the formation, wherein the conveying is via at least one of wireline and a string of tubulars.

The present disclosure also introduces a system comprising: means for obtaining in-situ: first optical spectral data associated with a formation fluid flowing through a downhole formation fluid sampling apparatus at a first time; and second optical spectral data associated with the formation fluid flowing through the downhole formation fluid sampling apparatus at a second time; and means for determining: a wavelength-independent scattering intensity within the formation fluid flowing through the downhole formation fluid sampling apparatus based on the first and second optical spectral data; and a wavelength-dependent scattering intensity within the formation fluid flowing through the downhole formation fluid sampling apparatus based on the first and second optical spectral data. The system may further comprise means for automatically adjusting an operating parameter associated with the downhole formation fluid sampling apparatus based on at least one of the determined wavelength-independent scattering intensity and the determined wavelength-dependent scattering intensity, wherein the adjusting means and the determining means may be communicably coupled. The determining means may comprise means for fitting the first and second optical spectral data with a wavelength-independent scattering coefficient and a wavelength-dependent scattering coefficient. The determining means may comprise means for determining a variance of the wavelength-independent scattering coefficient and the wavelength-dependent scattering coefficient in real-time. The determining means may comprise means for detecting at least one of: the variance of the wavelength-independent scattering coefficient exceeding a first predetermined threshold; and the variance of the wavelength-dependent scattering coefficient exceeding a second predetermined threshold. The determining means may comprise means for determining in real-time a semblance of the first and second optical spectral data before and after correcting the first and second optical spectral data based on the determined wavelength-independent scattering coefficient and the determined wavelength-dependent scattering coefficient.

The methodology introduced in the present disclosure has been described utilizing wavelength-dependent and wavelength-independent coefficients. However, one or more aspects of the present disclosure may be applicable or readily adaptable to other aspects and/or models of scattering to determine, combine and/or otherwise utilize the contributions of wavelength-scattering and wavelength-independent scattering. For example, the scope of the present disclosure may be applicable or readily adaptable to implementations in which scattering is accounted for other than as it is represented in optical density in Equation (3) above. Similar variances from the explicit description herein may also be within the scope of the present disclosure. Further, although the methodology has been described in terms of optical transmission measurements, the same methodology may be applied to any signal which responds to the presence of scatters in flowline fluid, in particular, optical backscattering signals and ultrasonic signals. Ultrasonic signals of varying frequencies can be used in place of optical signals of varying wavelengths and in place of measuring the optical density, the acoustic attenuation will be measured. However, the governing attenuation equations may be different.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

The Abstract at the end of this disclosure is provided to comply with 37 C.F.R. § 1.72(b) to allow the reader to quickly ascertain the nature of the technical disclosure. It is submitted with the understanding that it will not be used to interpret or limit the scope or meaning of the claims.

What is claimed is:

1. A method comprising:
  operating a downhole acquisition tool in a wellbore in a geological formation, wherein the wellbore or the geological formation, or both contain a fluid that comprises a native reservoir fluid of the geological formation and a contaminant;
  receiving a portion of the fluid into the downhole acquisition tool;
  measuring a fluid property of the fluid using the downhole acquisition tool, wherein the fluid property includes a first optical density of a first portion of the fluid at a first wavelength and a second optical density of a second portion of the fluid at a second wavelength, wherein the first and second optical densities are measured at successive times; and
  using one or more processors to:
    determine a scattering intensity of the first and second portions of the fluid using the first and second optical densities;
    estimate a saturation pressure of the fluid using the scattering intensity; and
    adjust an operational parameter of the downhole acquisition tool based on a relationship between the operational parameter and the saturation pressure;
  wherein determining the scattering intensity comprises using the processor to determine a wavelength-dependent scattering coefficient and a wavelength-independent scattering coefficient associated with each of the first and second optical densities;
  wherein estimating the saturation pressure of the fluid comprises determining whether oscillating features are present or absent in the wavelength-dependent scattering coefficient, the wavelength-independent scattering coefficient, or both; and
  wherein the one or more processors identify the saturation pressure to be above a flowline pressure of the downhole acquisition when the oscillating features are determined to be present, and wherein the one or more processors identify that the saturation pressure is below the flowline pressure when the oscillating features are determined to be absent.

2. The method of claim 1, wherein adjusting the operational parameter comprises increasing a flowline pressure of a flowline of the downhole acquisition tool when the flowline pressure is below the saturation pressure.

3. The method of claim 1, wherein the operational parameter comprises a pumping rate, output pressure, or both, of a pump configured to flow the fluid into the downhole acquisition tool.

4. The method of claim 1, wherein adjustment of the operational parameter is performed in proportion to the scattering intensity.

5. The method of claim 1, wherein the saturation pressure comprises a dew point, a bubble point pressure, or asphaltene onset pressure of the fluid.

6. The method of claim 1, wherein the first wavelength is different from the second wavelength.

7. A downhole fluid testing system comprising:
a downhole acquisition tool housing configured to be moved into a wellbore in a geological formation, wherein the wellbore or the geological formation, or both, contain fluid that comprises a native reservoir fluid of the geological formation and a contaminant;
a sensor disposed in the downhole acquisition tool housing that is configured to analyze portions of the fluid and obtain a first fluid property of the portions of the fluid, wherein the first fluid property includes a first optical density at a first wavelength and a second optical density at a second wavelength; and
a data processing system configured to determine a wavelength-dependent scattering coefficient and a wavelength-independent scattering coefficient for each of the first and second optical densities, to determine oscillating features of the wavelength-dependent scattering coefficient, the wavelength-independent scattering coefficient, or both, and to estimate the saturation pressure based on the oscillating features, wherein the oscillating features correspond to the scattering intensity, to estimate a saturation pressure of the fluid based at least in part on a scattering intensity of the first and second optical densities, and to adjust an operational parameter of the downhole acquisition tool based on a relationship between the operational parameter and the saturation pressure.

8. The system of claim 7, wherein the data processing system is disposed within the downhole acquisition tool housing, or outside the downhole acquisition tool housing at the surface, or both partly within the downhole acquisition tool housing and partly outside the downhole acquisition tool housing at the surface.

9. The system of claim 7, comprising a pump configured to control a pumping rate, an output pressure, or both of the fluid in a flowline of the downhole acquisition tool, wherein the operational parameter comprises the pumping rate or the output pressure of the pump.

10. The system of claim 9, wherein the data processing system is configured to adjust the pumping rate or the output pressure of the pump such that a flowline pressure in the flowline of the downhole acquisition tool increases when the flowline pressure is estimated to be below the saturation pressure.

11. The system of claim 7, wherein the sensor comprises a multi-channel optical sensor comprising a spectrometer configured to measure the first and second optical densities.

12. The system of claim 7, wherein the saturation pressure comprises a dew point, a bubble point pressure, or an asphaltene onset pressure of the fluid.

13. A non-transitory storage media comprising machine-readable instructions to:
receive a fluid parameter of a portion of fluid as analyzed by a downhole acquisition tool in a wellbore in a geological formation, wherein the wellbore or the geological formation, or both, contains the fluid, wherein the fluid comprises a mixture of native reservoir fluid of the geological formation and a contaminant, and wherein the fluid parameter includes a first optical density of a first portion of the fluid and a second optical density of a second portion of the fluid;
determine a scattering intensity of the first and second portions of the fluid;
determine a wavelength-dependent scattering coefficient and a wavelength-independent scattering coefficient for each of the first and second optical densities;
determine oscillating features of the wavelength-dependent scattering coefficient, the wavelength-independent scattering coefficient, or both, and to estimate the saturation pressure based on the oscillating features, wherein the oscillating features correspond to the scattering intensity;
estimate a saturation pressure of the fluid based on the scattering intensity; and
adjust an operational parameter of the downhole acquisition tool based on the saturation pressure.

14. The non-transitory storage media of claim 13, comprising instructions to adjust a pumping rate or an output pressure of a pump configured to flow the fluid into a flowline of the downhole acquisition tool such that a flowline pressure within the flowline increases when the flowline pressure is below the saturation pressure of the fluid.

15. The non-transitory storage media of claim 13, wherein the saturation pressure comprises a dew point, a bubble point pressure, or an asphaltene onset pressure.

* * * * *